US010556865B2

(12) United States Patent
Satchivi et al.

(10) Patent No.: US 10,556,865 B2
(45) **Date of Patent: *Feb. 11, 2020**

(54) SYNERGISTIC HERBICIDAL COMPOSITION CONTAINING CERTAIN PYRIDINE OR PYRIMIDINE CARBOXYLIC ACIDS AND CERTAIN CEREAL AND RICE HERBICIDES

(71) Applicant: Dow AgroSciences, LLC, Indianapolis, IN (US)

(72) Inventors: Norbert M. Satchivi, Westfield, IN (US); Paul R. Schmitzer, Indianapolis, IN (US); Carla N. Yerkes, Crawfordsville, IN (US); Terry R. Wright, Westfield, IN (US)

(73) Assignee: Dow AgroSciences LLC, Indianapolis, IN (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/671,671

(22) Filed: Aug. 8, 2017

(65) Prior Publication Data

US 2018/0022703 A1 Jan. 25, 2018

Related U.S. Application Data

(63) Continuation of application No. 12/196,697, filed on Aug. 22, 2008, now abandoned.

(60) Provisional application No. 60/966,340, filed on Aug. 27, 2007.

(51) Int. Cl.

| | |
|---|---|
| ***A01N 43/54*** | (2006.01) |
| ***A01N 43/40*** | (2006.01) |
| ***A01N 39/02*** | (2006.01) |
| ***A01N 25/32*** | (2006.01) |
| ***A01N 43/50*** | (2006.01) |
| ***A01N 43/56*** | (2006.01) |
| ***A01N 43/58*** | (2006.01) |
| ***A01N 43/653*** | (2006.01) |
| ***A01N 43/707*** | (2006.01) |
| ***A01N 43/82*** | (2006.01) |
| ***A01N 43/88*** | (2006.01) |
| ***A01N 43/90*** | (2006.01) |
| ***A01N 47/36*** | (2006.01) |
| ***A01N 47/38*** | (2006.01) |
| ***A01N 43/42*** | (2006.01) |
| ***A01N 47/30*** | (2006.01) |
| ***C07D 213/79*** | (2006.01) |

(52) U.S. Cl.

CPC .......... *C07D 213/79* (2013.01); *A01N 43/40* (2013.01); *A01N 43/42* (2013.01); *A01N 43/50* (2013.01); *A01N 43/54* (2013.01); *A01N 43/56* (2013.01); *A01N 43/58* (2013.01); *A01N 43/653* (2013.01); *A01N 43/707* (2013.01); *A01N 43/82* (2013.01); *A01N 43/88* (2013.01); *A01N 43/90* (2013.01); *A01N 47/30* (2013.01); *A01N 47/36* (2013.01); *A01N 47/38* (2013.01)

(58) Field of Classification Search

CPC combination set(s) only.
See application file for complete search history.

(56) References Cited

U.S. PATENT DOCUMENTS

| | | | | |
|---|---|---|---|---|
| 4,906,285 | A * | 3/1990 | Wada .................... | A01N 43/54 504/191 |
| 7,300,907 | B2 | 11/2007 | Epp et al. | |
| 7,314,849 | B2 | 1/2008 | Balko et al. | |
| 8,288,318 | B2 | 10/2012 | Epp et al. | |
| 8,530,383 | B2 * | 9/2013 | Satchivi ................ | A01N 25/32 504/110 |
| 8,652,999 | B1 | 2/2014 | Satchivi et al. | |
| 8,785,351 | B2 | 7/2014 | Mann et al. | |
| 8,791,048 | B2 | 7/2014 | Yerkes et al. | |
| 8,796,177 | B2 | 8/2014 | Mann et al. | |
| 8,809,232 | B2 | 8/2014 | Yerkes et al. | |
| 8,871,681 | B2 | 10/2014 | Mann et al. | |
| 8,883,682 | B2 | 11/2014 | Yerkes et al. | |
| 8,906,825 | B2 | 12/2014 | Mann et al. | |
| 8,906,826 | B2 | 12/2014 | Yerkes et al. | |
| 8,912,120 | B2 | 12/2014 | Yerkes et al. | |
| 8,912,121 | B2 | 12/2014 | Yerkes et al. | |
| 8,916,498 | B2 | 12/2014 | Yerkes et al. | |
| 8,916,499 | B2 | 12/2014 | Yerkes et al. | |
| 9,161,536 | B2 | 10/2015 | Bangel et al. | |
| 9,226,498 | B2 | 1/2016 | Degenhardt et al. | |
| 9,232,795 | B2 | 1/2016 | Bangel et al. | |
| 9,253,985 | B2 | 2/2016 | Hacker et al. | |
| 2007/0179060 | A1 | 8/2007 | Balko et al. | |

(Continued)

FOREIGN PATENT DOCUMENTS

| | | |
|---|---|---|
| CN | 1894220 | 1/2007 |
| WO | 2001051468 | 7/2001 |

(Continued)

OTHER PUBLICATIONS

Colby, S.R. Calculating synergistic and antagonistic responses of herbicide combinations. Weeds. vol. 15, pp. 20-22, 1967.
Richer, D.L. Synergism—a patent view. Pesticide Science. vol. 19, pp. 309-315, 1987.
Rummens, F.H.A. An improved definition of synergistic and antagonistic effects. Weed Science. vol. 23(1), pp. 4-6. 1975.
Webster's New World Dictionary, 2nd college ed., The World Publishing Co., New York, p. 1127, 1972.

(Continued)

*Primary Examiner* — John Pak
(74) *Attorney, Agent, or Firm* — Meunier Carlin & Curfman, LLC

(57) ABSTRACT

An herbicidal composition containing (a) a pyridine or pyrimidine carboxylic acid component and (b) a second cereal or rice herbicide component provides synergistic control of selected weeds.

13 Claims, No Drawings

(56) References Cited

U.S. PATENT DOCUMENTS

| | | | |
|---|---|---|---|
| 2009/0062121 | A1 | 3/2009 | Satchivi et al. |
| 2013/0310256 | A1 | 11/2013 | Yerkes et al. |
| 2014/0031213 | A1 | 1/2014 | Yerkes et al. |
| 2015/0218099 | A1 | 8/2015 | Mann |

FOREIGN PATENT DOCUMENTS

| | | |
|---|---|---|
| WO | 2005063721 | 7/2005 |
| WO | 2007082076 | 7/2007 |
| WO | 2007082098 | 7/2007 |
| WO | 2007120706 | 10/2007 |
| WO | 2008029518 | 3/2009 |

OTHER PUBLICATIONS

"Aminopyralid—new herbicide for pastures, roadsides, etc." Bob Hartzler. ISU Weed Science Online. 2006. Retrieved Mar. 21, 2016 from the Internet at URL: http://www.weeds.iastate.edu.mgmt/2006/aminopyralid.shtml.

European Search Report and Written Opinion issued in related EP Application No. 12162556.0 dated Jan. 4, 2013.

Intention to Grant issued in related EP Application No. 12162556.0 dated Jan. 23, 2015.

Decision to Grant issued in related EP Application No. 08798490.2 dated Oct. 24, 2013.

Office Action issued in related EP Application No. 08798490.2 dated Nov. 25, 2011.

Office Action issued in related EP Application No. 08798490.2 dated Dec. 10, 2010.

* cited by examiner

SYNERGISTIC HERBICIDAL COMPOSITION CONTAINING CERTAIN PYRIDINE OR PYRIMIDINE CARBOXYLIC ACIDS AND CERTAIN CEREAL AND RICE HERBICIDES

This application claims the benefit of U.S. Provisional Application 60/966,340 filed Aug. 27, 2007.

FIELD OF THE INVENTION

This invention concerns a synergistic herbicidal composition containing (a) an herbicidal pyridine or pyrimidine carboxylic acid component and (b) a cereal or rice herbicide component.

BACKGROUND OF THE INVENTION

The protection of crops from weeds and other vegetation which inhibit crop growth is a constantly recurring problem in agriculture. To help combat this problem, researchers in the field of synthetic chemistry have produced an extensive variety of chemicals and chemical formulations effective in the control of such unwanted growth. Chemical herbicides of many types have been disclosed in the literature and a large number are in commercial use.

In some cases, herbicidal active ingredients have been shown to be more effective in combination than when applied individually and this is referred to as "synergism." As described in the *Herbicide Handbook* of the Weed Science Society of America, Seventh Edition, 1994, p. 318, "'synergism' [is] an interaction of two or more factors such that the effect when combined is greater than the predicted effect based on the response of each factor applied separately." The present invention is based on the discovery that certain cereal or rice herbicides and certain pyridine or pyrimidine carboxylic acids, already known individually for their herbicidal efficacy, display a synergistic effect when applied in combination.

The herbicidal compounds forming the synergistic composition of this invention are independently known in the art for their effects on plant growth.

SUMMARY OF THE INVENTION

The present invention concerns a synergistic herbicidal mixture comprising an herbicidally effective amount of (a) a first herbicide selected from the group of a pyridine or a pyrimidine carboxylic acid of the formula (I)

(I)

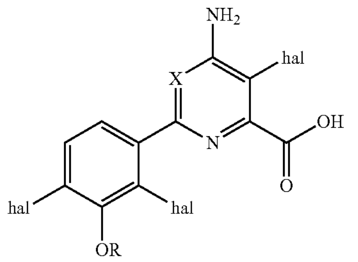

wherein X represents CH or N, hal represents F, Cl or Br, and R represents methyl or ethyl, and agriculturally acceptable salts, esters and amides of the carboxylic acid, and (b) a second herbicide selected from the group consisting of amidosulfuron, aminopyralid, beflubutamid, bensulfuron, bentazone, bispyribac, bromoxynil, carfentrazone, chlormequat, chlorsulfuron, chlorotoluron, clodinafop, clomazone, cyhalofop, dicamba, dichlorprop, diflufenican, diflufenzopyr, fenoxaprop, florasulam, flucarbazone, flufenacet, flupyrsulfuron, halosulfuron, indol-3-ylacetic acid, 4-indol-3-ylbutyric acid, imazamethabenz, imazamox, imazethapyr, iodosulfuron, isoproturon, isoxaben, MCPA, mesosulfuron, metribuzin, metsulfuron, norflurazon, penoxsulam, picolinafen, pinoxaden, propanil, propoxycarbazone, prosulfocarb, pyrasulfotole, pyrazosulfuron, pyriclor, pyroxsulam, quinclorac, sulcotrione, sulfosulfuron, thifensulfuron, tralkoxydim, tribenuron, triclopyr and mixtures thereof. The compositions may also contain an agriculturally acceptable adjuvant or carrier. The synergistic compositions may also generally be employed in combination with known herbicide safeners, particularly with cloquintocet mexyl.

Compounds of formula (I) in which X represents CH or N, hal represents F or Cl, and R represents methyl are independently preferred.

The present invention also concerns herbicidal compositions for and methods of controlling the growth of undesirable vegetation, particularly in wheat, rye, barley, oats, triticale and rice, and the use of these synergistic compositions.

The species spectra of the compounds of the synergistic mixture, i.e., the weed species which the respective compounds control, are broad and highly complimentary. For example, it has been surprisingly found that a combination of diflufenican, optionally with flufenacet, and a pyridine or pyrimidine carboxylic acid of the formula (I) exhibits a synergistic action in the control of blackgrass (*Alopecurus myosuroides* L; ALOMY), windgrass (*Apera spica-venti* L; APESV), wild oats (*Avena fatua* L; AVEFA), annual ryegrass (*Lolium multiflorum* L; LOLMG), lamb's-quarters (*Chenopodium album* L; CHEAL), wild mustard (*Sinapis arvensis* L SINAR), chickweed (*Stellaria media* L; STEME), scented mayweed (*Matricaria chamomila* L; MATCH) at application rates lower than the rates of the individual compounds.

It has also been surprisingly found that a mixture of an acetyl coenzyme A carboxylase-inhibiting herbicide such as clodinafop, fenoxaprop-P, pinoxaden or tralkoxydim, and a pyridine or pyrimidine carboxylic acid of the formula (I) exhibits a synergistic action in control of blackgrass (*Alopecurus myosuroides* L; ALOMY), windgrass (*Apera spica-venti* L; APESV), wild oats (*Avena fatua* L; AVEFA), annual ryegrass (*Lolium multiflorum* L; LOLMG), littleseed Canarygrass (*Phalaris minor* L; PHAMI) at application rates lower than the rates of the individual compounds.

The mixtures of an acetolactate synthase-inhibitor herbicide such as flupyrsulfuron, iodosulfuron, mesosulfuron, mesosulfuron plus iodosulfuron or sulfosulfuron of the sulfonylureas class; imazamethabenz of the imidazolinones class; propoxycarbazone of the sulfonylaminocarbonyltriazolinones class; pyroxsulam of the triazolopyrimidine class; and a pyridine or pyrimidine carboxylic acid of the formula (I) unexpectedly exhibit a synergistic action in control of blackgrass (*Alopecurus myosuroides* L; ALOMY), windgrass (*Apera spica-venti* L; APESV), wild oats (*Avena fatua* L; AVEFA), downy brome (*Bromus tectorum* L; BROTE), annual ryegrass (*Lolium multiflorum* L; LOLMG), Italian ryegrass (*Lolium multiflorum* L; LOLMU), rigid ryegrass (*Lolium rigidum* L; LOLRI), littleseed Canarygrass (*Phalaris minor* L; PHAMI), yellow foxtail (*Pennisetum americanum* L; PESGL), annual bluegrass (*Poa annua* L;

POAAN), green foxtail (*Setaria viridis* L; SETVI) at application rates lower than the rates of the individual compounds.

It has also been unexpectedly found that the mixture of an acetolactate synthase inhibiting herbicide such as amidosulfuron, chlorsulfuron, flupyrsulfuron, iodosulfuron, mesosulfuron, mesosulfuron plus iodosulfuron, metsulfuron, sulfosulfuron, thifensulfuron or tribenuron of the sulfonylureas class; propoxycarbazone or flucarbazone of the sulfonylaminocarbonyl-triazolinone class; imazamethabenz of the imidazolinones class; florasulam or pyroxsulam of the triazolopyrimidines class; and a pyridine or pyrimidine carboxylic acid of the formula (I) shows a synergistic action in control of canola (*Brassica napus* L; BRSNN), Canada thistle (*Cirsium arvense* L; CIRAR), chickweed (*Stellaria media* L; STEME), scented mayweed (*Matricaria chamomila* L; MATCH), bird's-eye speedwell (*Veronica persica* L; VERPE), wild pansy (*Viola tricolor* L; VIOTR), lady's-thumb (*Polygonum persicaria* L; POLPE), kochia (*Kochia scoparia* L; KCHSC) at application rates lower than the rates of the individual compounds.

The combination of a phytoene desaturase-inhibiting herbicide such as beflubutamid or picolinafen, and a pyridine or pyrimidine carboxylic acid of the formula (I) has resulted in an unexpected synergistic action in the control of kochia (*Kochia scoparia* L; KCHSC), wild mustard (*Sinapis arvensis* L; SINAR), ivy-leaved speedwell (*Veronica hederifolia* L; VERHE), bird's-eye speedwell (*Veronica persica* L; VERPE), wild pansy (*Viola tricolor* L; VIOTR), black mustard (*Brassica nigra* L; BRSNI), cut-leaf geranium (*Geranium dissectum* L; GERDI), wild buckwheat (*Polygonum convolvulus* L; POLCO), lady's-thumb (*Polygonum persicaria* L; POLPE), chickweed (*Stellaria media* L; STEME) at application rates lower than the rates of the individual compounds.

Surprisingly, the combinations of photosystem II-inhibiting herbicides such as bentazone, bromoxynil, chlorotoluron, isoproturon or metribuzin, and a pyridine or pyrimidine carboxylic acid of the formula (I) show a synergistic action in control of black mustard (*Brassica nigra* L; BRSNI), wild buckwheat (*Polygonum convolvulus* L; POLCO), chickweed (*Stellaria media* L; STEME), scented mayweed (*Matricaria chamomila* L; MATCH), bird's-eye speedwell (*Veronica persica* L; VERPE), wild pansy (*Viola tricolor* L; VIOTR), kochia (*Kochia scoparia* L; KCHSC), Russian thistle (*Salsola iberica* L; SASKR) at application rates lower than the rates of the individual compounds. It has been also surprisingly found that a combination of bromoxynil, optionally with pyrasulfotole, and a pyridine or pyrimidine carboxylic acid of the formula (I) shows a synergistic action in control of scented mayweed (*Matricaria chamomila* L; MATCH), bird's-eye speedwell (*Veronica persica* L; VERPE), wild pansy (*Viola tricolor* L; VIOTR), kochia (*Kochia scoparia* L; KCHSC) at application rates lower than the rates of the individual compounds.

The combination of a plant growth regulator such as chlormequat, indol-3-ylacetic acid or 4-indol-3-ylbutyric acid, and a pyridine or pyrimidine carboxylic acid of the formula (I) has resulted in an unexpected synergistic action in the control of kochia (*Kochia scoparia* L; KCHSC), black mustard (*Brassica nigra* L; BRSNI), cut-leaf geranium (*Geranium dissectum* L; GERDI), wild buckwheat (*Polygonum convolvulus* L; POLCO), chickweed (*Stellaria media* L; STEME), scented mayweed (*Matricaria chamomila* L; MATCH) at application rates lower than the rates of the individual compounds. Similarly, the mixtures of isoxaben, a cell wall biosynthesis inhibiting herbicide, or prosulfocarb, a lipid biosynthesis inhibiting herbicide, and a pyridine or pyrimidine carboxylic acid of the formula (I) have resulted in an unexpected synergistic action in the control of black mustard (*Brassica nigra* L; BRSNI), chickweed (*Stellaria media* L; STEME), scented mayweed (*Matricaria chamomila* L; MATCH), bird's-eye speedwell (*Veronica persica* L; VERPE), wild pansy (*Viola tricolor* L; VIOTR), Russian thistle (*Salsola iberica* L; SASKR) at application rates lower than the rates of the individual compounds.

It has also been unexpectedly found that the mixture of an auxinic herbicide such as aminopyralid, optionally with picolinafen or diflufenican, dicamba, dichlorprop-P, MCPA, quinclorac and a pyridine or pyrimidine carboxylic acid of the formula (I) exhibits a synergistic action in control of chickweed (*Stellaria media* L; STEME), scented mayweed (*Matricaria chamomila* L; MATCH), bird's-eye speedwell (*Veronica persica* L; VERPE), wild pansy (*Viola tricolor* L; VIOTR), lady's-thumb (*Polygonum persicaria* L; POLPE), kochia (*Kochia scoparia* L; KCHSC), black mustard (*Brassica nigra* L; BRSNI), cut-leaf geranium (*Geranium dissectum* L; GERDI), wild buckwheat (*Polygonum convolvulus* L; POLCO) at application rates lower than the rates of the individual compounds.

It has been also surprisingly found that the mixture of an EPSP (5-enolpyruvylshikimate-3-phosphate) synthase inhibitor herbicide such as glyphosate and a pyridine or pyrimidine carboxylic acid of the formula (I) exhibits a synergistic action in control of wild pansy (*Viola tricolor* L; VIOTR), kochia (*Kochia scoparia* L; KCHSC), Russian thistle (*Salsola iberica* L; SASKR) at application rates lower than the rates of the individual compounds.

4-Amino-3-chloro-6-(4-chloro-2-fluoro-3-methoxyphenyl)pyridine-2-carboxylic acid and 6-amino-5-chloro-2-(4-chloro-2-fluoro-3-methoxyphenyl) -pyrimidine-4-carboxylic acid derivatives are the especially preferred pyridine or pyrimidine carboxylic acids of the formula (I) for the control of weeds in cereal crops including spring, winter and durum wheat, spring and winter barley, oats, and triticale.

In rice culture (direct seeded, water seeded, or transplanted), the combination of an acetolactate synthase (ALS)-inhibiting herbicide such as penoxsulam of the triazolopyrimidine class; bispyribac-sodium of the pyrimidinylbenzoate chemical class; bensulfuron-methyl, halosulfuron-methyl, or pyrazosulfuron-ethyl of the sulfonylurea chemical class; or imazethapyr or imazamox of the imidazolinone chemical class; and a pyridine carboxylic acid of the formula (I) has resulted in an unexpected synergistic action in the control of *Ipomoea hederacea* (L.) JACQ. (IPOHE), *Echinochloa* species (ECHSS), *Ischaemum rugosum* SALISB. (ISCRU), *Leptochloa chinensis* (L.) NEES (LEFCH), *Cyperus esculentus* L. (CYPES), *Cyperus iria* L. (CYPIR), and *Eleocharis kuroguwai* OHWI (ELOKU) at application rates lower than the rates of the individual compounds. Glyphosate, an amino acid biosynthesis inhibitor which specifically inhibits 5-enolpyruvylshikimate-3-phosphate (EPSP) synthase, in combination with a pyridine carboxylic acid of the formula (I), produces synergistic activity on *Polygonum pensylvanicum* L. (POLPY), CYPES, CYPIR, *Digitaria sanguinalis* (L.) SCOP. (DIGSA), and LEFCH at application rates lower than the rates of the individual compounds. Synergistic activity between pyridine carboxylic acids of the formula (I) in combination with compounds of the imidazolinone chemistry class or in combination with glyphosate will be particularly useful in crops where imidazolinone or glyphosate resistant crop varieties are being employed.

It has also been surprising that a mixture of propanil, a photosystem (PS) II-inhibiting herbicide and a pyridine carboxylic acid of the formula (I) exhibits a synergistic action in control of IPOHE and *Polygonum persicaria* L. (POLPE), at application rates lower than the rates of the individual compounds and an increased speed of activity on CYPIR and *Scirpus maritimus* L. (SCPMA) over that observed with effective control rates of the individual compounds. Similarly, a mixture of carfentrazone-ethyl, a protoporphyrinogen IX oxidase (PROTOX) inhibiting herbicide, and a pyridine carboxylic acid of the formula (I) exhibits a synergistic action in control POLPE, CYPES, and CYPIR at application rates lower than the rates of the individual compounds as well as an increased speed of activity on CYPES.

It has also been unexpectedly found that the mixture of cyhalofop-butyl, an acetyl coenzyme A carboxylase (ACCase) inhibiting herbicide, and a pyridine carboxylic acid of the formula (I) shows a synergistic action in the control of POLPY, *Sphenoclea zeylanica* GAERTN. (SPDZE), ECHSS, LEFCH, *Cyperus* species (CYPSS), *Fimbristylis miliacea* (L.) VAHL (FIMMI), and *Scirpus* species (SCPSS) at application rates lower than the rates of the individual compounds, while a mixture of fenoxaprop-p-ethyl, another ACCase-inhibiting herbicide, and a pyridine carboxylic acid of the formula (I) shows a synergistic action in control of FIMMI and SCPSS at application rates lower than the rates of the individual compounds.

The combination of an auxinic herbicide such as triclopyr, MCPA, or quinclorac and a pyridine carboxylic acid of the formula (I) has resulted in an unexpected synergistic action in the control of *Marsilea crenata* PRESL (MASCR), CYPSS, FIMMI, ECHSS, LEFCH, *Brachiaria platyphylla* (BRISEB.) NASH (BRAPP), and ISCRU at application rates lower than the rates of the individual compounds. Similarly, the combination of an auxin transport inhibitor such as diflufenzopyr and a pyridine carboxylic acid of the formula (I) has resulted in an unexpected synergistic action in the control of IPOHE, LEFCH, and CYPIR at application rates lower than the rates of the individual compounds.

The combination of compounds with bleaching modes of action such as clomazone; norflurazon, a phytoene desaturase inhibiting herbicide; sulcotrione, a p-hydroxyphenylpyruvate dioxygenase (HPPD) inhibiting herbicide; or pyriclor and a pyridine carboxylic acid of the formula (I) has resulted in an unexpected synergistic action in the control of BRAPP, DIGSA, ECHSS, LEFCH, CYPSS, FIMMI, and SCPMA at application rates lower than the rates of the individual compounds.

4-Amino-3-chloro-6-(4-chloro-2-fluoro-3-methoxyphenyl)pyridine-2-carboxylic acid derivatives, 4-amino-3-chloro-6-(2,4-dichloro-3-methoxyphenyl) -pyridine-2-carboxylic acid derivatives, and 4-amino-3-chloro-6-(4-chloro-2-fluoro-3-ethoxyphenyl)pyridine-2-carboxylic acid derivatives are the especially preferred pyridine carboxylic acids of the formula (I) for the control of weeds in transplanted, water seeded, and direct seeded rice.

DETAILED DESCRIPTION OF THE INVENTION

The pyridine and pyrimidine carboxylic acids are a new class of compounds having herbicidal activity. A number of pyridine and pyrimidine carboxylic acid compounds are described in U.S. Pat. Nos. 7,300,907 (B2) and 7,314,849 (B2), including 6-amino-5-chloro-2-(4-chloro-2-fluoro-3-methoxyphenyl)pyrimidine-4-carboxylic acid methyl ester, 4-amino-3-chloro-6-(4-chloro-2-fluoro-3-methoxyphenyl) pyridine-2-carboxylic acid methyl ester and 4-amino-3-chloro-6-(2,4-dichloro-3-methoxyphenyl)pyridine-2-carboxylic acid methyl ester. The pyridine or pyrimidine carboxylic acid of the formula (I) controls annual grass weeds including *Setaria, Pennisetum*, and *Echinochloa*; broadleaf weeds such as *Papaver, Galium, Lamium, Kochia, Amaranthus, Aeschynomene, Sesbania*, and *Monochoria*; and sedge species such as *Cyperus* and *Scirpus*.

Amidosulfuron is the common name for N-[[[[(4,6-dimethoxy-2-pyrimidinyl)amino]carbonyl]amino]sulfonyl]-N-methylmethanesulfonamide. Its herbicidal activity is described in *The Pesticide Manual*, Fourteenth Edition, 2006. Amidosulfuron controls a wide range of broadleaf weeds, particularly cleavers.

Aminopyralid is the common name for 4-amino-3,6-dichloro-2-pyridinecarboxylic acid. Its herbicidal activity is described in *The Pesticide Manual*, Fourteenth Edition, 2006 Aminopyralid controls annual and perennial broadleaf weeds in grassland.

Beflubutamid is the common name for 2-[4-fluoro-3-(trifluoromethyl) -phenoxy]-N-(phenylmethyl)butanamide. Its herbicidal activity is described in *The Pesticide Manual*, Fourteenth Edition, 2006. Beflubutamid provides pre—and early post—emergence control of broadleaf weeds in wheat and barley.

Bensulfuron is the common name for 2-[[[[[(4,6-dimethoxy-2-pyrimidinyl)amino]carbonyl]amino]sulfonyl] methyl]benzoic acid. Its herbicidal activity is described in *The Pesticide Manual*, Fourteenth Edition, 2006. Bensulfuron-methyl controls annual and perennial weeds and sedges in flooded or wetland rice.

Bentazone is the common name for 3-(1-methylethyl)-1H-2,1,3-benzothiadiazin-4(3H)-one 2,2-dioxide. Its herbicidal activity is described in *The Pesticide Manual*, Fourteenth Edition, 2006. Bentazone controls broadleaf weeds in spring and winter cereals.

Bispyribac is the common name for 2,6-bis[(4,6-dimethoxy-2-pyrimidinyl)oxy]benzoic acid. Its herbicidal activity is described in *The Pesticide Manual*, Fourteenth Edition, 2006. Bispyribac-sodium controls grasses, sedges and broadleaf weeds in direct-seeded rice.

Bromoxynil is the common name for 3,5-dibromo-4-hydroxybenzonitrile. Its herbicidal activity is described in *The Pesticide Manual*, Fourteenth Edition, 2006. Bromoxynil is used for the post-emergence control of annual broadleaf weeds.

Carfentrazone is the common name for α,2-dichloro-5-[4-(difluoromethyl)-4,5-dihydro-3-methyl-5-oxo-1H-1,2,4-triazol-1-yl]-4-fluorobenzenepropanoic acid. Its herbicidal activity is described in *The Pesticide Manual*, Fourteenth Edition, 2006. Carfentrazone-ethyl controls a wide range of broadleaf weeds in cereals and rice.

Chlormequat is the common name for 2-chloro-N,N,N-trimethyl-ethanaminium chloride. Its herbicidal activity is described in *The Pesticide Manual*, Fourteenth Edition, 2006. Chlormequat is a plant growth regulator for producing sturdier plants.

Chlorsulfuron is the common name for 2-chloro-N-[[(4-methoxy-6-methyl-1,3,5-triazin-2-yl)amino]carbonyl]benzenesulfonamide. Its herbicidal activity is described in *The Pesticide Manual*, Fourteenth Edition, 2006. Chlorsulfuron controls a wide range of broadleaf weeds and some annual grasses.

Chlorotoluron is the common name for N'-(3-chloro-4-methylphenyl)-N,N-dimethylurea. Its herbicidal activity is described in *The Pesticide Manual*, Fourteenth Edition, 2006. Chlorotoluron controls a wide range of broadleaf weeds and some annual grasses in winter cereals.

Clodinafop is the common name for (2R)-2-[4-[(5-chloro-3-fluoro-2-pyridinyl)oxy]phenoxy]propanoic acid. Its herbicidal activity is described in *The Pesticide Manual*, Fourteenth Edition, 2006. Clodinafop controls a wide range of annual grasses.

Clomazone is the common name for 2-[(2-chlorophenyl) methyl]-4,4-dimethyl-3-isoxazolidinone. Its herbicidal activity is described in *The Pesticide Manual*, Fourteenth Edition, 2006. Clomazone controls grass weeds and broadleaf weeds.

Cyhalofop is the common name for (2R)-2-[4-(4-cyano-2-fluorophenoxy) -phenoxy]propanoic acid. Its herbicidal activity is described in *The Pesticide Manual*, Fourteenth Edition, 2006. Cyhalofop-butyl controls grass weeds in rice.

Dicamba is the common name for 3,6-dichloro-2-methoxybenzoic acid. Its herbicidal activity is described in *The Pesticide Manual*, Fourteenth Edition, 2006. Dicamba controls annual and perennial broadleaf weeds in cereals.

Dichlorprop P is the common name for (2R)-2-(2,4-dichlorophenoxy) propanoic acid. Its herbicidal activity is described in *The Pesticide Manual*, Fourteenth Edition, 2006. Dichlorprop controls a wide range of annual and perennial broadleaf weeds in cereals and grassland.

Diflufenican is the common name for N-(2,4-difluorophenyl)-2-[3-(trifluoromethyl)phenoxy]-3-pyridinecarboxamide. Its herbicidal activity is described in *The Pesticide Manual*, Fourteenth Edition, 2006. Diflufenican controls annual grass weeds and certain broadleaf weeds including *Galium, Veronica* and *Viola* spp.

Diflufenzopyr is the common name for 2-[1-[[[(3,5-difluorophenyl) -amino]carbonyl]hydrazono]ethyl]-3-pyridinecarboxylic acid. Its herbicidal activity is described in *The Pesticide Manual*, Fourteenth Edition, 2006. Diflufenzopyr controls annual and perennial broadleaf weeds.

Fenoxaprop is the common name for 2-[4-[(6-chloro-2-benzoxazolyl) -oxy]phenoxy]propanoic acid. Its herbicidal activity is described in *The Pesticide Manual*, Fourteenth Edition, 2006. Fenoxaprop controls a wide range of annual and perennial grasses.

Florasulam is the common name for N-(2,6-difluorophenyl)-8-fluoro-5-methoxy[1,2,4]triazolo[1,5-c]pyrimidine-2-sulfonamide. Its herbicidal activity is described in *The Pesticide Manual*, Fourteenth Edition, 2006. Florasulam controls broadleaf weeds, especially *Galium aparine, Stellaria media, Polygonum convolvulus, Matricaria* spp. and various cruciferae.

Flucarbazone is the common name for 4,5-dihydro-3-methoxy-4-methyl-5-oxo-N-[[2-(trifluoromethoxy)phenyl] sulfonyl]-1H-1,2,4-triazole-1-carboxamide. Its herbicidal activity is described in *The Pesticide Manual*, Fourteenth Edition, 2006. Flucarbazone controls grass weeds, especially *Avena fatua* and *Setaria viridis* and some broadleaf weeds.

Flufenacet is the common name for N-(4-fluorophenyl)-N-(1-methylethyl) -2-[[5-(trifluoromethyl)-1,3,4-thiadiazol-2-yl]oxy]acetamide. Its herbicidal activity is described in *The Pesticide Manual*, Fourteenth Edition, 2006. Flufenacet controls a broad spectrum of grass weeds and certain broadleaf weeds.

Flupyrsulfuron is the common name for 2-[[[[(4,6-dimethoxy-2-pyrimidinyl)amino]carbonyl]amino]sulfonyl]-6-(trifluoromethyl)-3-pyridinecarboxylic acid. Its herbicidal activity is described in *The Pesticide Manual*, Fourteenth Edition, 2006. Flupyrsulfuron controls black-grass and some broadleaf weeds.

Glyphosate is the common name for N-(phosphonomethyl)glycine. Its herbicidal activity is described in *The Pesticide Manual*, Fourteenth Edition, 2006. Glyphosate controls a wide range of annual and perennial, broadleaf and grass weeds.

Halosulfuron is the common name for 3-chloro-5-[[[[(4,6-dimethoxy-2-pyrimidinyl)amino]carbonyl]amino]sulfonyl]-1-methyl-1H-pyrazole-4-carboxylic acid. Its herbicidal activity is described in *The Pesticide Manual*, Fourteenth Edition, 2006. Halosulfuron-methyl controls annual broadleaf weeds and nutsedge in rice.

Imazamethabenz is the common name for 2-[4,5-dihydro-4-methyl-4-(1-methylethyl)-5-oxo-1H-imidazol-2-yl]-4(or 5)-methylbenzoic acid. Its herbicidal activity is described in *The Pesticide Manual*, Fourteenth Edition, 2006. Imazamethabenz controls *Alopecurus, Apera* and *Avena* in wheat, barley and rye.

Imazamox is the common name for 2-[4,5-dihydro-4-methyl-4-(1-methylethyl)-5-oxo-1H-imidazol-2-yl]-5-(methoxymethyl)-3-pyridinecarboxylic acid. Its herbicidal activity is described in *The Pesticide Manual*, Fourteenth Edition, 2006. Imazamox is used for broad spectrum weed control in a variety of crops.

Imazethapyr is the common name for 2-[4,5-dihydro-4-methyl-4-(1-methylethyl)-5-oxo-1H-imidazol-2-yl]-5-ethyl-3-pyridinecarboxylic acid. Its herbicidal activity is described in *The Pesticide Manual*, Fourteenth Edition, 2006. Imazethapyr controls annual and perennial grass and broadleaf weeds.

Indol-3-ylacetic acid is the common name for 1H-indole-3-acetic acid. Its plant growth regulating activity is described in *The Pesticide Manual*, Fourteenth Edition, 2006.

4-Indol-3-ylbutyric acid is the common name for 1H-indole-3-butanoic acid. Its plant growth regulating activity is described in *The Pesticide Manual*, Fourteenth Edition, 2006.

Iodosulfuron is the common name for 4-iodo-2-[[[[(4-methoxy-6-methyl -1,3,5-triazin-2-yl)amino]carbonyl] amino]sulfonyl]benzoic acid. Its herbicidal activity is described in *The Pesticide Manual*, Fourteenth Edition, 2006. Iodosulfuron controls grass and broadleaf weeds.

Isoproturon is the common mane for N,N-dimethyl-N'-[4-(1-methylethyl)phenyl]urea. Its herbicidal activity is described in *The Pesticide Manual*, Fourteenth Edition, 2006. Isoproturon controls a wide range of annual broadleaf and grass weeds in cereals other than durum wheat.

Isoxaben is the common name for N-[3-(1-ethyl-1-methylpropyl)-5-isoxazolyl]-2,6-dimethoxybenzamide. Its herbicidal activity is described in *The Pesticide Manual*, Fourteenth Edition, 2006. Isoxaben pre-emergently controls broadleaf weeds in cereals.

MCPA is (4-chloro-2-methylphenoxy)acetic acid. Its herbicidal activity is described in *The Pesticide Manual*, Fourteenth Edition, 2006. MCPA controls annual and perennial broadleaf weeds in crops including cereals.

Mesosulfuron is the common name for 2-[[[[(4,6-dimethoxy-2-pyrimidinyl)amino]carbonyl]amino]sulfonyl]-4-[[(methylsulfonyl)amino]-methyl]benzoic acid. Its herbicidal activity is described in *The Pesticide Manual*, Fourteenth Edition, 2006. Mesosulfuron controls grass and some broadleaf weeds.

Metribuzin is the common name for 4-amino-6-(1,1-dimethylethyl)-3-(methylthio)-1,2,4-triazin-5(4H)-one. Its herbicidal activity is described in *The Pesticide Manual*, Fourteenth Edition, 2006. Metribuzin controls many grasses and broadleaf weeds in cereals.

Metsulfuron is the common name for 2-[[[[(4-methoxy-6-methyl-1,3,5-triazin-2-yl)amino]carbonyl]amino]sulfonyl]benzoic acid. Its herbicidal activity is described in *The Pesticide Manual*, Fourteenth Edition, 2006. Metsulfuron controls a wide range of grass and broadleaf weeds in wheat, barley, rice and oats.

Norflurazon, is the common name for 4-chloro-5-(methylamino)-2-[3-(trifluoromethyl)phenyl]-3(2H)-pyridazinone. Its herbicidal activity is described in *The Pesticide Manual*, Fourteenth Edition, 2006. Norflurazon is used for the pre-emergence control of grasses and sedges, as well as some broadleaf weeds.

Penoxsulam is the common name for 2-(2,2-difluoroethoxy)-N-(5,8-dimethoxy[1,2,4]triazolo[1,5-c]pyrimidin-2-yl)-6-(trifluoromethyl) -benzenesulfonamide. Its herbicidal activity is described in *The Pesticide Manual*, Fourteenth Edition, 2006. Penoxsulam controls broadleaf, sedge, and aquatic weeds and *Echinochloa* spp. in rice.

Picolinafen is the common name for N-(4-fluorophenyl)-6-[3-(trifluoromethyl)phenoxy]-2-pyridinecarboxamide. Its herbicidal activity is described in *The Pesticide Manual*, Fourteenth Edition, 2006. Picolinafen controls broadleaf weeds, especially *Galium, Viola, Lamium* and *Veronica* spp.

Pinoxaden is the common name for 8-(2,6-diethyl-4-methylphenyl) -1,2,4,5-tetrahydro-7-oxo-7H-pyrazolo[1,2-d][1,4,5]oxadiazepin-9-yl 2,2-dimethylpropanoate. Its herbicidal activity is described in *The Pesticide Manual*, Fourteenth Edition, 2006. Pinoxaden controls annual grasses, including *Alopecurus, Apera, Avena, Lolium, Phalaris* and *Setaria.*

Propanil is the common name for N-(3,4-dichlorophenyl) propanamide. Its herbicidal activity is described in *The Pesticide Manual*, Fourteenth Edition, 2006. Propanil controls grass and broadleaf weeds in rice.

Propoxycarbazone is the common name for methyl 2-[[[(4,5-dihydro-4-methyl-5-oxo-3-propoxy-1H-1,2,4-triazol-1-yl)carbonyl]amino]sulfonyl]benzoate. Its herbicidal activity is described in *The Pesticide Manual*, Fourteenth Edition, 2006. Propoxycarbazone controls annual and some perennial grasses, including *Bromus* spp., *Alopecurus myosuroides, Apera spica-venti*, and *Elymus repens*, and some broadleaf weeds.

Prosulfocarb is the common name for S-(phenylmethyl) dipropylcarbamo-thioate. Its herbicidal activity is described in *The Pesticide Manual*, Fourteenth Edition, 2006. Prosulfocarb controls a wide range of grass and broadleaf weeds in wheat, barley and rye.

Pyrasulfotole is the common name for (5-hydroxy-1,3-dimethyl-1H -pyrazol-4-yl)[2-(methylsulfonyl)-4-(trifluoromethyl)phenyl]methanone. Pyrasulfotole controls a broad spectrum of broadleaf weeds in cereals.

Pyrazosulfuron is the common name for 5-[[[[(4,6-dimethoxy-2-pyrimidinyl)amino]carbonyl]amino]sulfonyl]-1-methyl-1H-pyrazole-4-carboxylic acid. Its herbicidal activity is described in *The Pesticide Manual*, Fourteenth Edition, 2006. Pyrazosulfuron-ethyl controls annual and perennial broadleaf weeds and sedges in rice.

Pyriclor is the common name for 2,3,5-trichloro-4-pyridinol.

Pyroxsulam is the common name for N-(5,7-dimethoxy [1,2,4]triazolo[1,5-α]pyrimidin-2-yl)-2-methoxy-4-(trifluoromethyl)-3-pyridinesulfonamide. Pyroxsulam controls grass and broadleaf weeds.

Quinclorac is the common name for 3,7-dichloro-8-quinolinecarboxylic acid. Its herbicidal activity is described in *The Pesticide Manual*, Fourteenth Edition, 2006. Quinclorac controls weeds in transplanted and direct-seeded rice.

Sulcotrione is the common name for 2-[2-chloro-4-(methylsulfonyl)benzoyl]-1,3-cyclohexanedione. Its herbicidal activity is described in *The Pesticide Manual*, Fourteenth Edition, 2006. Sulcotrione controls grass and broadleaf weeds.

Sulfosulfuron is the common name for N-[[(4,6-dimethoxy-2-pyrimidinyl)amino]carbonyl]-2-(ethylsulfonyl)imidazo[1,2-a]pyridine-3-sulfonamide. Its herbicidal activity is described in *The Pesticide Manual*, Fourteenth Edition, 2006. Sulfosulfuron controls annual grasses and broadleaf weeds.

Thifensulfuron is the common name for 3-[[[[(4-methoxy-6-methyl-1,3,5-triazin-2-yl)amino]carbonyl] amino]sulfonyl]-2-thiophenecarboxylic acid. Its herbicidal activity is described in *The Pesticide Manual*, Fourteenth Edition, 2006. Thifensulfuron controls a wide range of annual weeds.

Tralkoxydim is the common name 2-[1-(ethoxyimino) propyl]-3-hydroxy -5-(2,4,6-trimethylphenyl)-2-cyclohexen-1-one. Its herbicidal activity is described in *The Pesticide Manual*, Fourteenth Edition, 2006. Tralkoxydim controls annual grasses, including *Avena* spp., *Lolium* spp., *Setaria viridis, Phalaris* spp., *Alopecurus myosuroides* and *Apera spica-venti.*

Tribenuron is the common name 2-[[[[(4-methoxy-6-methyl-1,3,5-triazin -2-yl)methylamino]carbonyl]amino] sulfonyl]benzoic acid. Its herbicidal activity is described in *The Pesticide Manual*, Fourteenth Edition, 2006. Tribenuron controls broadleaf weeds.

Triclopyr is the common name for [(3,5,6-trichloro-2-pyridinyl)oxy]acetic acid. Its herbicidal activity is described in *The Pesticide Manual*, Fourteenth Edition, 2006. Triclopyr controls broadleaf weeds in rice.

The term herbicide is used herein to mean an active ingredient that kills, controls or otherwise adversely modifies the growth of plants. An herbicidally effective or vegetation controlling amount is an amount of active ingredient which causes an adversely modifying effect and includes deviations from natural development, killing, regulation, desiccation, retardation, and the like. The terms plants and vegetation include germinant seeds, emerging seedlings, plants emerging from vegetative propagules, and established vegetation.

Herbicidal activity is exhibited by the compounds of the synergistic mixture when they are applied directly to the plant or to the locus of the plant at any stage of growth or before planting or emergence. The effect observed depends upon the plant species to be controlled, the stage of growth of the plant, the application parameters of dilution and spray drop size, the particle size of solid components, the environmental conditions at the time of use, the specific compound employed, the specific adjuvants and carriers employed, the soil type, and the like, as well as the amount of chemical applied. These and other factors can be adjusted as is known in the art to promote non-selective or selective herbicidal action. Generally, it is preferred to apply the composition of the present invention postemergence to relatively immature undesirable vegetation to achieve the maximum control of weeds.

In the composition of this invention, the weight ratio of the pyridine or pyrimidine carboxylic acid of formula (I) component to the second cereal or rice herbicide component at which the herbicidal effect is synergistic lies within the range of between about 5:1 and about 1:256.

The rate at which the synergistic composition is applied will depend upon the particular type of weed to be controlled, the degree of control required, and the timing and method of application. In general, the composition of the invention can be applied at an application rate of between about 8 grams per hectare (g/ha) and about 1200 g/ha based on the total amount of active ingredients in the composition. Depending upon the particular cereal or rice herbicide used, the cereal or rice herbicide component is applied at a rate between about 4 g/ha and about 1120 g/ha and the pyridine or pyrimidine carboxylic acid of formula (I) component is applied at a rate between about 4 g/ha and about 70 g/ha The components of the synergistic mixture of the present invention can be applied either separately or as part of a multipart herbicidal system.

The synergistic mixture of the present invention can be applied in conjunction with one or more other herbicides to control a wider variety of undesirable vegetation. When used in conjunction with other herbicides, the composition can be formulated with the other herbicide or herbicides, tank mixed with the other herbicide or herbicides or applied sequentially with the other herbicide or herbicides. Some of the herbicides that can be employed in conjunction with the synergistic composition of the present invention include: amide herbicides such as allidochlor, benzadox, benzipram, bromobutide, cafenstrole, CDEA, chlorthiamid, cyprazole, dimethenamid, dimethenamid-P, diphenamid, epronaz, etnipromid, fentrazamide, flupoxam, fomesafen, halosafen, isocarbamid, napropamide, naptalam, pethoxamid, propyzamide, quinonamid and tebutam; anilide herbicides such as chloranocryl, cisanilide, clomeprop, cypromid, etobenzanid, fenasulam, flufenican, mefenacet, mefluidide, metamifop, monalide, naproanilide and pentanochlor; arylalanine herbicides such as benzoylprop, flamprop and flamprop-M; chloroacetanilide herbicides such as acetochlor, alachlor, butachlor, butenachlor, delachlor, diethatyl, dimethachlor, metazachlor, metolachlor, S-metolachlor, pretilachlor, propachlor, propisochlor, prynachlor, terbuchlor, thenylchlor and xylachlor; sulfonanilide herbicides such as benzofluor, perfluidone, pyrimisulfan and profluazol; sulfonamide herbicides such as asulam, carbasulam, fenasulam and oryzalin; antibiotic herbicides such as bilanafos; benzoic acid herbicides such as chloramben, 2,3,6-TBA and tricamba; pyrimidinyloxybenzoic acid herbicides such as pyriminobac; pyrimidinylthiobenzoic acid herbicides such as pyrithiobac; phthalic acid herbicides such as chlorthal; picolinic acid herbicides such as clopyralid and picloram; quinolinecarboxylic acid herbicides such as quinmerac; arsenical herbicides such as cacodylic acid, CMA, DSMA, hexaflurate, MAA, MAMA, MSMA, potassium arsenite and sodium arsenite; benzoylcyclohexanedione herbicides such as mesotrione, tefuryltrione and tembotrione; benzofuranyl alkylsulfonate herbicides such as benfuresate and ethofumesate; carbamate herbicides such as asulam, carboxazole chlorprocarb, dichlormate, fenasulam, karbutilate and terbucarb; carbanilate herbicides such as barban, BCPC, carbasulam, carbetamide, CEPC, chlorbufam, chlorpropham, CPPC, desmedipham, phenisopham, phenmedipham, phenmedipham-ethyl, propham and swep; cyclohexene oxime herbicides such as alloxydim, butroxydim, clethodim, cloproxydim, cycloxydim, profoxydim, sethoxydim and tepraloxydim; cyclopropylisoxazole herbicides such as isoxachlortole and isoxaflutole; dicarboximide herbicides such as benzfendizone, cinidon-ethyl, flumezin, flumiclorac, flumioxazin and flumipropyn; dinitroaniline herbicides such as benfluralin, butralin, dinitramine, ethalfluralin, fluchloralin, isopropalin, methalpropalin, nitralin, oryzalin, pendimethalin, prodiamine, profluralin and trifluralin; dinitrophenol herbicides such as dinofenate, dinoprop, dinosam, dinoseb, dinoterb, DNOC, etinofen and medinoterb; diphenyl ether herbicides such as ethoxyfen; nitrophenyl ether herbicides such as acifluorfen, aclonifen, bifenox, chlomethoxyfen, chlornitrofen, etnipromid, fluorodifen, fluoroglycofen, fluoronitrofen, fomesafen, furyloxyfen, halosafen, lactofen, nitrofen, nitrofluorfen and oxyfluorfen; dithiocarbamate herbicides such as dazomet and metam; halogenated aliphatic herbicides such as alorac, chloropon, dalapon, flupropanate, hexachloroacetone, iodomethane, methyl bromide, monochloroacetic acid, SMA and TCA; imidazolinone herbicides such as imazapic, imazapyr and imazaquin; inorganic herbicides such as ammonium sulfamate, borax, calcium chlorate, copper sulfate, ferrous sulfate, potassium azide, potassium cyanate, sodium azide, sodium chlorate and sulfuric acid; nitrile herbicides such as bromobonil, chloroxynil, dichlobenil, iodobonil, ioxynil and pyraclonil; organophosphorus herbicides such as amiprofos-methyl, anilofos, bensulide, bilanafos, butamifos, 2,4-DEP, DMPA, EBEP, fosamine, glufosinate, glyphosate and piperophos; phenoxy herbicides such as bromofenoxim, clomeprop, 2,4-DEB, 2,4-DEP, difenopenten, disul, erbon, etnipromid, fenteracol and trifopsime; phenoxyacetic herbicides such as 4-CPA, 2,4-D, 3,4-DA, MCPA-thioethyl and 2,4,5-T; phenoxybutyric herbicides such as 4-CPB, 2,4-DB, 3,4-DB, MCPB and 2,4,5-TB; phenoxypropionic herbicides such as cloprop, 4-CPP, 3,4-DP, fenoprop, mecoprop and mecoprop-P; aryloxyphenoxypropionic herbicides such as chlorazifop, clofop, diclofop, fenthiaprop, fluazifop, fluazifop-P, haloxyfop, haloxyfop-P, isoxapyrifop, metamifop, propaquizafop, quizalofop, quizalofop-P and trifop; phenylenediamine herbicides such as dinitramine and prodiamine; pyrazolyl herbicides such as benzofenap, pyrazolynate, pyrazoxyfen, pyroxasulfone and topramezone; pyrazolylphenyl herbicides such as fluazolate and pyraflufen; pyridazine herbicides such as credazine, pyridafol and pyridate; pyridazinone herbicides such as brompyrazon, chloridazon, dimidazon, flufenpyr, metflurazon, oxapyrazon and pydanon; pyridine herbicides such as aminopyralid, cliodinate, clopyralid, dithiopyr, fluroxypyr, haloxydine, picloram and thiazopyr; pyrimidinediamine herbicides such as iprymidam and tioclorim; quaternary ammonium herbicides such as cyperquat, diethamquat, difenzoquat, diquat, morfamquat and paraquat; thiocarbamate herbicides such as butylate, cycloate, di-allate, EPTC, esprocarb, ethiolate, isopolinate, methiobencarb, molinate, orbencarb, pebulate, pyributicarb, sulfallate, thiobencarb, tiocarbazil, tri-allate and vernolate; thiocarbonate herbicides such as dimexano, EXD and proxan; thiourea herbicides such as methiuron; triazine herbicides such as dipropetryn, triaziflam and trihydroxytriazine; chlorotriazine herbicides such as atrazine, chlorazine, cyanazine, cyprazine, eglinazine, ipazine, mesoprazine, procyazine, proglinazine, propazine, sebuthylazine, simazine, terbuthylazine and trietazine; methoxytriazine herbicides such as atraton, methometon, prometon, secbumeton, simeton and terbumeton; methylthiotriazine herbicides such as ametryn, aziprotryne, cyanatryn, desmetryn, dimethametryn, methoprotryne, prometryn, simetryn and terbutryn; triazinone herbicides such as ametridione, amibuzin, hexazinone, isomethiozin and metamitron; triazole herbicides such as amitrole, cafenstrole, epronaz and flupoxam; triazolone herbicides such as amicarbazone, bencarbazone, sulfentrazone and thiencarbazone-methyl; triazolopyrimidine herbicides such as cloransulam, diclosulam, flumetsulam and metosulam; uracil herbicides such as butafenacil, bromacil, flupropacil, isocil, lenacil and terbacil; 3-phenyluracils; urea herbicides such as benzthiazuron, cumyluron, cycluron, dichloralurea, isonoruron, isouron, methabenzthiazuron, monisouron and noruron; phenylurea herbicides such as anisuron, buturon, chlorbromuron, chloreturon, chloroxuron, daimuron, difenoxuron, dimefuron, diuron, fenuron, fluometuron, fluothiuron, linuron, methiuron, methyldymron, metobenzuron, metobromuron, metoxuron, monolinuron, monuron, neburon, parafluron, phenobenzuron, siduron, tetrafluron and thidiazuron; pyrimidinylsulfonylurea herbicides such as azimsulfuron, chlorimuron, cyclosulfamuron, ethoxysulfuron, flazasulfuron, flucetosulfuron, foramsulfuron, imazosulfuron, nicosulfuron, orthosulfamuron, oxasulfuron, primisulfuron, rimsulfuron, sulfometuron and trifloxysulfuron; triazinylsulfonylurea herbicides such as cinosulfuron, ethametsulfuron, metsulfuron, prosulfuron, triasulfuron, triflusulfuron and tritosulfuron; thiadiazolylurea herbicides such as buthiuron, ethidimuron, tebuthiuron, thiazafluron and thidiazuron; and unclassified herbicides such as acrolein, allyl alcohol, azafenidin, benazolin, benzobicyclon, buthidazole, calcium cyanamide, cambendichlor, chlorfenac, chlorfenprop, chlorflurazole, chlorflurenol, cinmethylin, CPMF, cresol, orthodichlorobenzene, dimepiperate, endothal, fluoromidine, fluridone, flurochloridone, flurtamone, fluthiacet, indanofan, methazole, methyl isothiocyanate, nipyraclofen, OCH, oxadiargyl, oxadiazon, oxaziclomefone, pentachlorophenol, pentoxazone, phenylmercury acetate, prosulfalin, pyribenzoxim, pyriftalid, quinoclamine, rhodethanil, sulglycapin, thidiazimin, tridiphane, trimeturon, tripropindan and tritac.

The synergistic composition of the present invention can, further, be used in conjunction with glyphosate, glufosinate, dicamba, imidazolinones or 2,4-D on glyphosate-tolerant, glufosinate-tolerant, dicamba-tolerant, imidazolinone-tolerant or 2,4-D-tolerant crops. It is generally preferred to use the synergistic composition of the present invention in combination with herbicides that are selective for the crop being treated and which complement the spectrum of weeds controlled by these compounds at the application rate employed. It is further generally preferred to apply the synergistic composition of the present invention and other complementary herbicides at the same time, either as a combination formulation or as a tank mix.

The synergistic composition of the present invention can generally be employed in combination with known herbicide safeners, such as benoxacor, benthiocarb, brassinolide, cloquintocet (mexyl), cyometrinil, daimuron, dichlormid, dicyclonon, dimepiperate, disulfoton, fenchlorazole-ethyl, fenclorim, flurazole, fluxofenim, furilazole, isoxadifen-ethyl, mefenpyr-diethyl, MG 191, MON 4660, naphthalic anhydride (NA), oxabetrinil, R29148 and N-phenyl-sulfonylbenzoic acid amides, to enhance their selectivity. Cloquintocet (mexyl) is a particularly preferred safener for the synergistic compositions of the present invention, specifically antagonizing any harmful effect of the synergistic compositions on rice and cereals.

In practice, it is preferable to use the synergistic composition of the present invention in mixtures containing an herbicidally effective amount of the herbicidal components along with at least one agriculturally acceptable adjuvant or carrier. Suitable adjuvants or carriers should not be phytotoxic to valuable crops, particularly at the concentrations employed in applying the compositions for selective weed control in the presence of crops, and should not react chemically with herbicidal components or other composition ingredients. Such mixtures can be designed for application directly to weeds or their locus or can be concentrates or formulations that are normally diluted with additional carriers and adjuvants before application. They can be solids, such as, for example, dusts, granules, water dispersible granules, or wettable powders, or liquids, such as, for example, emulsifiable concentrates, solutions, emulsions or suspensions.

Suitable agricultural adjuvants and carriers that are useful in preparing the herbicidal mixtures of the invention are well known to those skilled in the art.

Liquid carriers that can be employed include water, toluene, xylene, petroleum naphtha, crop oil, acetone, methyl ethyl ketone, cyclohexanone, trichloroethylene, perchloroethylene, ethyl acetate, amyl acetate, butyl acetate, propylene glycol monomethyl ether and diethylene glycol monomethyl ether, methanol, ethanol, isopropanol, amyl alcohol, ethylene glycol, propylene glycol, glycerine, N-methyl-2-pyrrolidinone, N,N-dimethyl alkylamides, dimethyl sulfoxide, liquid fertilizers and the like. Water is generally the carrier of choice for the dilution of concentrates.

Suitable solid carriers include talc, pyrophyllite clay, silica, attapulgus clay, kaolin clay, kieselguhr, chalk, diatomaceous earth, lime, calcium carbonate, bentonite clay, Fuller's earth, cotton seed hulls, wheat flour, soybean flour, pumice, wood flour, walnut shell flour, lignin, and the like.

It is usually desirable to incorporate one or more surface-active agents into the compositions of the present invention. Such surface-active agents are advantageously employed in both solid and liquid compositions, especially those designed to be diluted with carrier before application. The surface-active agents can be anionic, cationic or nonionic in character and can be employed as emulsifying agents, wetting agents, suspending agents, or for other purposes. Typical surface-active agents include salts of alkyl sulfates, such as diethanol-ammonium lauryl sulfate; alkylarylsulfonate salts, such as calcium dodecyl-benzenesulfonate; alkylphenol-alkylene oxide addition products, such as nonylphenol-$C_{18}$ ethoxylate; alcohol-alkylene oxide addition products, such as tridecyl alcohol-$C_{16}$ ethoxylate; soaps, such as sodium stearate; alkylnaphthalene-sulfonate salts, such as sodium dibutylnaphthalenesulfonate; dialkyl esters of sulfosuccinate salts, such as sodium di(2-ethylhexyl) sulfosuccinate; sorbitol esters, such as sorbitol oleate; quaternary amines, such as lauryl trimethyl-ammonium chloride; polyethylene glycol esters of fatty acids, such as poly-ethylene glycol stearate; block copolymers of ethylene oxide and propylene oxide; and salts of mono and dialkyl phosphate esters.

Other adjuvants commonly used in agricultural compositions include compatibilizing agents, antifoam agents, sequestering agents, neutralizing agents and buffers, corrosion inhibitors, dyes, odorants, spreading agents, penetration aids, sticking agents, dispersing agents, thickening agents, freezing point depressants, antimicrobial agents, and the like. The compositions may also contain other compatible components, for example, other herbicides, plant growth regulants, fungicides, insecticides, and the like and can be formulated with liquid fertilizers or solid, particulate fertilizer carriers such as ammonium nitrate, urea and the like.

The concentration of the active ingredients in the synergistic composition of the present invention is generally from 0.001 to 98 percent by weight. Concentrations from 0.01 to 90 percent by weight are often employed. In compositions designed to be employed as concentrates, the active ingredients are generally present in a concentration from 5 to 98 weight percent, preferably 10 to 90 weight percent. Such compositions are typically diluted with an inert carrier, such as water, before application. The diluted compositions usually applied to weeds or the locus of weeds generally contain 0.0001 to 1 weight percent active ingredient and preferably contain 0.001 to 0.05 weight percent.

The present compositions can be applied to weeds or their locus by the use of conventional ground or aerial dusters, sprayers, and granule applicators, by addition to irrigation or paddy water, and by other conventional means known to those skilled in the art.

The following examples illustrate the present invention.

Examples

Evaluation of Postemergence Herbicidal Activity of Mixtures in Cereal Crops

Seeds of the desired test plant species were planted in Sun Gro MetroMix® 306 planting mixture, which typically has a pH of 6.0 to 6.8 and an organic matter content of about 30 percent, in plastic pots with a surface area of 103.2 square centimeters ($cm^2$). When required to ensure good germination and healthy plants, a fungicide treatment and/or other chemical or physical treatment was applied. The plants were grown for 7-36 days in a greenhouse with an approximate 14 hour photoperiod which was maintained at about 18° C. during the day and 17° C. during the night. Nutrients and water were added on a regular basis and supplemental lighting was provided with overhead metal halide 1000-Watt lamps as necessary. The plants were employed for testing when they reached the second or third true leaf stage.

Treatments consisted of compound (as listed in Tables 1 through 64) and a second cereal herbicide alone and in combination. Weighed amounts of esters (methyl) or salts (TEA [triethylammonium], K [potassium]) of 4-amino-3-chloro -6-(4-chloro-2-fluoro-3-methoxyphenyl)pyridine-2-carboxylic acid (Compound A) or of 6-amino-5-chloro-2-(4-chloro-2-fluoro-3-methoxyphenyl)pyrimidine-4-carboxylic acid (Compound B), were placed in 25 milliliter (mL) glass vials and dissolved in a volume of 97:3 v/v acetone/DMSO to obtain 4.5 milligrams (mg) active ingredient (ai)/mL stock solutions. If the experimental compound did not dissolve readily, the mixture was warmed and/or sonicated. The concentrated stock solutions were diluted to 1.5 mg ai/mL with the addition of 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. A dilution solution was prepared by mixing 1 volume of 97:3 v/v acetone/DMSO and 2 volumes of an aqueous mixture containing acetone, water, isopropyl alcohol, DMSO, Agri-dex crop oil concentrate, and Triton® X-77 surfactant in a 64.7:26.0:6.7:2.0:0.7:0.01 v/v ratio. Compound requirements are based upon a 12 mL application volume at a rate of 187 liters per hectare (L/ha). Spray solutions of the second cereal herbicide and experimental compound mixtures were prepared by adding the stock solutions to the appropriate amount of dilution solution to form 12 mL spray solution with active ingredients in two- and three-way combinations. Formulated compounds were applied to the plant material with an overhead Mandel track sprayer equipped with 8002E nozzles calibrated to deliver 187 L/ha over an application area of 0.503 square meters ($m^2$) at a spray height of 18 inches (43 cm) above average plant canopy. Control plants were sprayed in the same manner with the solvent blank.

The treated plants and control plants were placed in a greenhouse as described above and watered by sub-irrigation to prevent wash-off of the test compounds. After 20-22 days, the condition of the test plants as compared with that of the control plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$\text{Expected}=A+B-(A\times B/100)$$

A=observed efficacy of active ingredient A at the same concentration as used in the mixture.

B=observed efficacy of active ingredient B at the same concentration as used in the mixture.

Some of the compounds tested, application rates employed, plant species tested, and results are given in Table 1 through Table 64.

TABLE 1

Synergistic Activity of Herbicidal Compositions on Several Key Grass Weeds in Cereal Crops

| Application Rate (g/ha) | | ALOMY | | APESV | | AVEFA | | LOLMG | | SETVI | |
|---|---|---|---|---|---|---|---|---|---|---|---|
| Compound A Methyl | Diflufenican | Ob | Ex | Ob | Ex | Ob | Ex | Ob | Ex | Ob | Ex |
| 17.5 | 0 | 0 | — | 20 | — | 30 | — | 20 | — | 70 | — |
| 35 | 0 | 20 | — | 20 | — | 30 | — | 40 | — | 75 | — |
| 70 | 0 | 50 | — | 30 | — | 35 | — | 0 | — | 80 | — |
| 0 | 15 | 0 | — | 0 | — | 0 | — | 0 | — | 0 | — |
| 17.5 | 15 | 30 | 0 | 30 | 20 | 30 | 30 | 40 | 20 | 80 | 70 |
| 35 | 15 | 40 | 20 | 20 | 20 | 35 | 30 | 55 | 40 | 85 | 75 |
| 70 | 15 | 55 | 50 | 50 | 30 | 55 | 35 | 65 | 60 | 90 | 80 |

TABLE 2

Synergistic Activity of Herbicidal Compositions on Several Key Grass Weeds in Cereal Crops

| Application Rate (g/ha) | | ALOMY | | LOLMG | |
|---|---|---|---|---|---|
| Compound A Methyl | Liberator* | Ob | Ex | Ob | Ex |
| 17.5 | 0 | 0 | — | 20 | — |
| 35 | 0 | 20 | — | 40 | — |
| 70 | 0 | 50 | — | 60 | — |

TABLE 2-continued

Synergistic Activity of Herbicidal Compositions on Several Key Grass Weeds in Cereal Crops

| Application Rate (g/ha) | | ALOMY | | LOLMG | |
|---|---|---|---|---|---|
| Compound A Methyl | Liberator* | Ob | Ex | Ob | Ex |
| 0 | 75 | 0 | — | 0 | — |
| 17.5 | 75 | 30 | 0 | 40 | 20 |
| 35 | 75 | 30 | 20 | 45 | 40 |
| 70 | 75 | 45 | 50 | 50 | 60 |

*Liberator contains 100 g ai/l diflufenican and 400 g ai/l flufenacet

TABLE 3

Synergistic Activity of Herbicidal Compositions on Several Key Grass Weeds in Cereal Crops

| Application Rate (g/ha) | | | ALOMY | | APESV | | AVEFA | | PHAMI | |
|---|---|---|---|---|---|---|---|---|---|---|
| Compound A Methyl | Pinoxaden | Cloquintocet-mexyl | Ob | Ex | Ob | Ex | Ob | Ex | Ob | Ex |
| 35 | 0 | 0 | 30 | — | 10 | — | 40 | — | 30 | — |
| 70 | 0 | 0 | 30 | — | 10 | — | 45 | — | 35 | — |
| 0 | 7.5 | 1.875 | 53 | — | 70 | — | 30 | — | 25 | — |
| 0 | 15 | 3.75 | 93 | — | 93 | — | 93 | — | 85 | — |
| 35 | 7.5 | 1.875 | 85 | 67 | 90 | 73 | 80 | 58 | 85 | 48 |
| 70 | 7.5 | 1.875 | 90 | 67 | 80 | 73 | 85 | 62 | 85 | 51 |
| 35 | 15 | 3.75 | 100 | 95 | 90 | 93 | 100 | 96 | 90 | 90 |
| 70 | 15 | 3.75 | 95 | 95 | 85 | 93 | 100 | 96 | 90 | 90 |

TABLE 4

Synergistic Activity of Herbicidal Compositions on Several Key Grass Weeds in Cereal Crops

| Application Rate (g/ha) | | | ALOMY | | APESV | | AVEFA | | PHAMI | |
|---|---|---|---|---|---|---|---|---|---|---|
| Compound A Methyl | Clodinafop-propargyl | Cloquintocet-mexyl | Ob | Ex | Ob | Ex | Ob | Ex | Ob | Ex |
| 17.5 | 0 | 0 | 0 | — | 0 | — | 0 | — | 20 | — |
| 35 | 0 | 0 | 30 | — | 10 | — | 40 | — | 30 | — |
| 70 | 0 | 0 | 30 | — | 10 | — | 45 | — | 35 | — |
| 0 | 7 | 1.75 | 30 | — | 20 | — | 15 | — | 13 | — |
| 0 | 14 | 3.5 | 80 | — | 33 | — | 78 | — | 40 | — |
| 17.5 | 7 | 1.75 | 95 | 30 | 90 | 20 | 90 | 15 | 80 | 30 |
| 35 | 7 | 1.75 | 80 | 51 | 30 | 28 | 70 | 49 | 65 | 39 |
| 70 | 7 | 1.75 | 85 | 51 | 30 | 28 | 75 | 53 | 60 | 43 |
| 17.5 | 14 | 3.5 | 95 | 80 | 90 | 33 | 99 | 78 | 85 | 52 |
| 35 | 14 | 3.5 | 90 | 86 | 30 | 39 | 90 | 87 | 75 | 58 |
| 70 | 14 | 3.5 | 85 | 86 | 30 | 39 | 90 | 88 | 75 | 61 |

TABLE 5

Synergistic Activity of Herbicidal Compositions on Several Key Grass Weeds in Cereal Crops

| Application Rate (g/ha) | | | ALOMY | | APESV | | AVEFA | | PHAMI | |
|---|---|---|---|---|---|---|---|---|---|---|
| Compound A Methyl | Fenoxaprop-p | Mefenpyr-diethyl | Ob | Ex | Ob | Ex | Ob | Ex | Ob | Ex |
| 17.5 | 0 | 0 | 0 | — | 0 | — | 0 | — | 20 | — |
| 35 | 0 | 0 | 30 | — | 10 | — | 40 | — | 30 | — |
| 70 | 0 | 0 | 30 | — | 10 | — | 45 | — | 35 | — |

TABLE 5-continued

Synergistic Activity of Herbicidal Compositions on Several Key Grass Weeds in Cereal Crops

| Application Rate (g/ha) | | | | | | | | | | |
|---|---|---|---|---|---|---|---|---|---|---|
| Compound | Fenoxaprop- | Mefenpyr- | ALOMY | | APESV | | AVEFA | | PHAMI | |
| A Methyl | p | diethyl | Ob | Ex | Ob | Ex | Ob | Ex | Ob | Ex |
| 0 | 11.5 | 3.13 | 25 | — | 15 | — | 10 | — | 5 | — |
| 0 | 23 | 6.27 | 68 | — | 73 | — | 35 | — | 58 | — |
| 17.5 | 11.5 | 3.13 | 80 | 25 | 95 | 15 | 90 | 10 | 80 | 24 |
| 35 | 11.5 | 3.13 | 90 | 48 | 80 | 24 | 85 | 46 | 40 | 34 |
| 70 | 11.5 | 3.13 | 75 | 48 | 85 | 24 | 90 | 51 | 45 | 38 |
| 17.5 | 23 | 6.27 | 85 | 68 | 95 | 73 | 95 | 35 | 95 | 66 |
| 35 | 23 | 6.27 | 95 | 77 | 95 | 75 | 90 | 61 | 90 | 70 |
| 70 | 23 | 6.27 | 85 | 77 | 95 | 75 | 95 | 64 | 95 | 72 |

TABLE 6

Synergistic Activity of Herbicidal Compositions on Several Key Grass Weeds in Cereal Crops

| Application Rate (g/ha) | | | | | |
|---|---|---|---|---|---|
| Compound A | | ALOMY | | PHAMI | |
| Methyl | Tralkoxydim | Ob | Ex | Ob | Ex |
| 17.5 | 0 | 0 | — | 20 | — |
| 35 | 0 | 30 | — | 30 | — |
| 70 | 0 | 30 | — | 35 | — |
| 0 | 25 | 78 | — | 35 | — |
| 0 | 50 | 70 | — | 45 | — |
| 17.5 | 25 | 90 | 78 | 20 | 48 |
| 35 | 25 | 90 | 84 | 65 | 55 |
| 70 | 25 | 80 | 84 | 65 | 58 |
| 17.5 | 50 | 85 | 70 | 40 | 56 |
| 35 | 50 | 100 | 79 | 65 | 62 |
| 70 | 50 | 95 | 79 | 65 | 64 |

TABLE 7

Synergistic Activity of Herbicidal Compositions on Several Key Grass Weeds in Cereal Crops

| Application Rate (g/ha) | | | | | |
|---|---|---|---|---|---|
| Compound A | | ALOMY | | SETVI | |
| Methyl | Iodosulfuron | Ob | Ex | Ob | Ex |
| 35 | 0 | 3 | — | 77 | — |
| 70 | 0 | 20 | — | 82 | — |
| 140 | 0 | 47 | — | 91 | — |
| 0 | 2.5 | 50 | — | 0 | — |
| 35 | 2.5 | 83 | 52 | 70 | 77 |
| 70 | 2.5 | 73 | 60 | 89 | 82 |
| 140 | 2.5 | 80 | 73 | 97 | 91 |

TABLE 8

Synergistic Activity of Herbicidal Compositions on Several Key Grass Weeds in Cereal Crops

| Application Rate (g/ha) | | | |
|---|---|---|---|
| Compound A | | BROTE | |
| Methyl | Mesosulfuron | Ob | Ex |
| 35 | 0.0 | 0.0 | — |
| 70 | 0.0 | 0.0 | — |

TABLE 8-continued

Synergistic Activity of Herbicidal Compositions on Several Key Grass Weeds in Cereal Crops

| Application Rate (g/ha) | | | |
|---|---|---|---|
| Compound A | | BROTE | |
| Methyl | Mesosulfuron | Ob | Ex |
| 140 | 0.0 | 13 | — |
| 0 | 3.8 | 73 | — |
| 35 | 3.8 | 73 | 73 |
| 70 | 3.8 | 77 | 73 |
| 140 | 3.8 | 82 | 77 |

TABLE 9

Synergistic Activity of Herbicidal Compositions on Several Key Grass Weeds in Cereal Crops

| Application Rate (g/ha) | | | | | |
|---|---|---|---|---|---|
| Compound A | | BROTE | | POAAN | |
| Methyl | Atlantis WG* | Ob | Ex | Ob | Ex |
| 35 | 0 | 0 | — | 0 | — |
| 70 | 0 | 0 | — | 3 | — |
| 140 | 0 | 13 | — | 3 | — |
| 0 | 4 | 67 | — | 50 | — |
| 35 | 4 | 75 | 67 | 57 | 50 |
| 70 | 4 | 77 | 67 | 53 | 52 |
| 140 | 4 | 80 | 71 | 53 | 52 |

*Atlantis WG contains 30 g/kg mesosulfuron and 6 g/kg iodosulfuron and 90 g/kg mefenpyr-diethyl

TABLE 10

Synergistic Activity of Herbicidal Compositions on Several Key Grass Weeds in Cereal Crops

| Application Rate (g/ha) | | | | | | | |
|---|---|---|---|---|---|---|---|
| Compound | Propoxy- | BROTE | | LOLMU | | POAAN | |
| A Methyl | carbazone-Na | Ob | Ex | Ob | Ex | Ob | Ex |
| 35 | 0 | 0 | — | 3 | — | 0 | — |
| 70 | 0 | 0 | — | 20 | — | 3 | — |
| 140 | 0 | 13 | — | 40 | — | 3 | — |
| 0 | 25 | 92 | — | 17 | — | 7 | — |
| 35 | 25 | 95 | 92 | 50 | 19 | 37 | 7 |
| 70 | 25 | 96 | 92 | 53 | 33 | 37 | 10 |
| 140 | 25 | 94 | 93 | 53 | 50 | 37 | 10 |

TABLE 11

Synergistic Activity of Herbicidal Compositions on Several Key Grass Weeds in Cereal Crops

| Application Rate (g/ha) | | PHAMI | |
|---|---|---|---|
| Compound A Methyl | Pyroxsulam* | Ob | Ex |
| 35 | 0.0 | 3 | — |
| 70 | 0.0 | 6 | — |
| 140 | 0.0 | 17 | — |
| 0 | 3.8 | 78 | — |
| 35 | 3.8 | 84 | 79 |
| 70 | 3.8 | 89 | 80 |
| 140 | 3.8 | 92 | 82 |

*Pyroxsulam contains 30 g ai/l pyroxsulam and 90 g ai/l cloquintocet-mexyl

TABLE 12

Synergistic Activity of Herbicidal Compositions on Several Key Grass Weeds in Cereal Crops

| Application rate (g/ha) | | LOLRI | |
|---|---|---|---|
| Compound A TEA | Flupyrsulfuron | Ob | Ex |
| 35 | 0 | 0 | — |
| 70 | 0 | 0 | — |
| 140 | 0 | 10 | — |
| 0 | 5 | 0 | — |
| 35 | 5 | 15 | 0 |
| 70 | 5 | 10 | 0 |
| 140 | 5 | 10 | 10 |

TABLE 13

Synergistic Activity of Herbicidal Compositions on Several Key Grass Weeds in Cereal Crops

| Application rate (g/ha) | | LOLMG | | LOLRI | | LOLMU | | PHAMI | |
|---|---|---|---|---|---|---|---|---|---|
| Compound A TEA | Imazamethabenz | Ob | Ex | | Ex | | Ex | | Ex |
| 35 | 0 | 0 | — | 0 | — | 0 | — | 0 | — |
| 70 | 0 | 0 | — | 0 | — | 0 | — | 0 | — |
| 140 | 0 | 0 | — | 10 | — | 0 | — | 0 | — |
| 0 | 125 | 0 | — | 0 | — | 0 | — | 0 | — |
| 35 | 125 | 10 | 0 | 10 | 0 | 10 | 0 | 20 | 0 |
| 70 | 125 | 10 | 0 | 10 | 0 | 10 | 0 | 10 | 0 |
| 140 | 125 | 10 | 0 | 10 | 10 | 10 | 0 | 0 | 0 |

TABLE 14

Synergistic Activity of Herbicidal Compositions on Several Key Grass Weeds in Cereal Crops

| Application rate (g/ha) | | ALOMY | | APESV | | AVEFA | | LOLMU | |
|---|---|---|---|---|---|---|---|---|---|
| Compound A TEA | Iodosulfuron | Ob | Ex | Ob | Ex | Ob | Ex | Ob | Ex |
| 35 | 0 | 0 | — | 8 | — | 0 | — | 0 | — |
| 70 | 0 | 0 | — | 13 | — | 0 | — | 3 | — |
| 140 | 0 | 3 | — | 15 | — | 0 | — | 3 | — |
| 0 | 2.5 | 50 | — | 68 | — | 35 | — | 53 | — |
| 35 | 2.5 | 53 | 50 | 91 | 70 | 60 | 35 | 65 | 53 |

TABLE 14-continued

Synergistic Activity of Herbicidal Compositions on Several Key Grass Weeds in Cereal Crops

| Application rate (g/ha) | | ALOMY | | APESV | | AVEFA | | LOLMU | |
|---|---|---|---|---|---|---|---|---|---|
| Compound A TEA | Iodosulfuron | Ob | Ex | Ob | Ex | Ob | Ex | Ob | Ex |
| 70 | 2.5 | 60 | 50 | 87 | 72 | 50 | 35 | 74 | 54 |
| 140 | 2.5 | 70 | 51 | 94 | 73 | 64 | 35 | 59 | 54 |

TABLE 15

Synergistic Activity of Herbicidal Compositions on Several Key Grass Weeds in Cereal Crops

| Application rate (g/ha) | | APESV | | BROTE | |
|---|---|---|---|---|---|
| Compound A TEA | Mesosulfuron | Ob | Ex | Ob | Ex |
| 35 | 0 | 3 | — | 0 | — |
| 70 | 0 | 0 | — | 0 | — |
| 140 | 0 | 4 | — | 0 | — |
| 0 | 3.75 | 93 | — | 75 | — |
| 35 | 3.75 | 96 | 93 | 78 | 75 |
| 70 | 3.75 | 95 | 93 | 78 | 75 |
| 140 | 3.75 | 96 | 93 | 76 | 75 |

TABLE 16

Synergistic Activity of Herbicidal Compositions on Several Key Grass Weeds in Cereal Crops

| Application rate (g/ha) | | ALOMY | | APESV | | BROTE | | PHAMI | | POAAN | |
|---|---|---|---|---|---|---|---|---|---|---|---|
| Compound A TEA | Atlantis WG* | Ob | Ex | Ob | Ex | Ob | Ex | Ob | Ex | Ob | Ex |
| 35 | 0 | 0 | — | 3 | — | 0 | — | 0 | — | 0 | — |
| 70 | 0 | 0 | — | 0 | — | 0 | — | 0 | — | 0 | — |
| 140 | 0 | 0 | — | 4 | — | 0 | — | 0 | — | 0 | — |
| 0 | 3.6 | 95 | — | 96 | — | 73 | — | 97 | — | 63 | — |
| 35 | 3.6 | 96 | 95 | 98 | 96 | 75 | 73 | 99 | 97 | 64 | 63 |
| 70 | 3.6 | 95 | 95 | 97 | 96 | 75 | 73 | 99 | 97 | 65 | 63 |
| 140 | 3.6 | 97 | 95 | 98 | 96 | 78 | 73 | 99 | 97 | 69 | 63 |

*Atlantis WG contains 30 g/kg mesosulfuron and 6 g/kg iodosulfuron and 90 g/kg mefenpyr-diethyl

TABLE 17

Synergistic Activity of Herbicidal Compositions on Several Key Grass Weeds in Cereal Crops

| Application rate (g/ha) | | APESV | | AVEFA | | LOLRI | | LOLMU | | POAAN | |
|---|---|---|---|---|---|---|---|---|---|---|---|
| Compound A TEA | Propoxycarbazone-sodium | Ob | Ex | Ob | Ex | Ob | Ex | Ob | Ex | Ob | Ex |
| 35 | 0 | 3 | — | 0 | — | 0 | — | 0 | — | 0 | — |
| 70 | 0 | 0 | — | 3 | — | 0 | — | 0 | — | 0 | — |
| 140 | 0 | 4 | — | 8 | — | 10 | — | 5 | — | 0 | — |
| 0 | 25 | 90 | — | 76 | — | 10 | — | 15 | — | 5 | — |
| 35 | 25 | 93 | 90 | 76 | 76 | 10 | 10 | 24 | 15 | 8 | 5 |
| 70 | 25 | 92 | 90 | 81 | 76 | 25 | 10 | 30 | 15 | 8 | 5 |
| 140 | 25 | 92 | 90 | 87 | 77 | 30 | 19 | 29 | 19 | 8 | 5 |

TABLE 18

Synergistic Activity of Herbicidal Compositions on Several Key Grass Weeds in Cereal Crops

| Application rate (g/ha) | | | | | | | | | | | | |
|---|---|---|---|---|---|---|---|---|---|---|---|---|
| Compound A | | ALOMY | | APESV | | AVEFA | | BROTE | | PHAMI | |
| TEA | Pyroxsulam* | Ob | Ex | Ob | Ex | Ob | Ex | Ob | Ex | Ob | Ex |
| 35 | 0 | 0 | — | 8 | — | 0 | — | 0 | — | 0 | — |
| 70 | 0 | 0 | — | 13 | — | 0 | — | 3 | — | 0 | — |
| 140 | 0 | 3 | — | 15 | — | 0 | — | 3 | — | 0 | — |
| 0 | 3.75 | 89 | — | 96 | — | 91 | — | 85 | — | 76 | — |
| 35 | 3.75 | 95 | 89 | 99 | 97 | 93 | 91 | 88 | 85 | 90 | 76 |
| 70 | 3.75 | 96 | 89 | 99 | 97 | 92 | 91 | 88 | 85 | 91 | 76 |
| 140 | 3.75 | 95 | 89 | 99 | 97 | 92 | 91 | 88 | 85 | 91 | 76 |

*Pyroxsulam contains 30 g ai/l pyroxsulam and 90 g ai/l cloquintocet-mexyl

TABLE 19

Synergistic Activity of Herbicidal Compositions on Several Key Grass Weeds in Cereal Crops

| Application rate (g/ha) | | | | | |
|---|---|---|---|---|---|
| Compound A | | ALOMY | | LOLRI | |
| TEA | Sulfosulfuron | Ob | Ex | | Ex |
| 35 | 0 | 0 | — | 0 | — |
| 70 | 0 | 0 | — | 0 | — |
| 140 | 0 | 0 | — | 10 | — |
| 0 | 8.75 | 85 | — | 10 | — |
| 35 | 8.75 | 95 | 85 | 30 | 10 |
| 70 | 8.75 | 90 | 85 | 20 | 10 |
| 140 | 8.75 | 85 | 85 | 10 | 19 |

TABLE 20

Synergistic Activity of Herbicidal Compositions on Several Key Grass Weeds in Cereal Crops

| Application Rate (g/ha) | | | | | | | | | | |
|---|---|---|---|---|---|---|---|---|---|---|
| Compound | | Cloquintocet- | ALOMY | | APESV | | AVEFA | | PHAMI | |
| B Methyl | Pinoxaden | mexyl | Ob | Ex | Ob | Ex | Ob | Ex | Ob | Ex |
| 8.75 | 0 | 0 | 0 | — | 0 | — | 0 | — | 0 | — |
| 17.5 | 0 | 0 | 10 | — | 0 | — | 0 | — | 0 | — |
| 35 | 0 | 0 | 20 | — | 0 | — | 0 | — | 0 | — |
| 70 | 0 | 0 | 40 | — | 0 | — | 0 | — | 0 | — |
| 0 | 15 | 3.75 | 80 | — | 85 | — | 90 | — | 85 | — |
| 8.75 | 15 | 3.75 | 90 | 80 | 90 | 85 | 100 | 90 | 95 | 85 |
| 17.5 | 15 | 3.75 | 90 | 82 | 90 | 85 | 95 | 90 | 95 | 85 |
| 35 | 15 | 3.75 | 95 | 84 | 90 | 85 | 95 | 90 | 95 | 85 |
| 70 | 15 | 3.75 | 90 | 88 | 90 | 85 | 95 | 90 | 95 | 85 |

TABLE 21

Synergistic Activity of Herbicidal Compositions on Several Key Grass Weeds in Cereal Crops

| Application Rate (g/ha) | | | | | | | | | | | | | | |
|---|---|---|---|---|---|---|---|---|---|---|---|---|---|---|
| Compound | Fenoxaprop- | Mefenpyr- | ALOMY | | APESV | | AVEFA | | LOLMG | | PESGL | | PHAMI | |
| B Methyl | p ethyl | diethyl | Ob | Ex | Ob | Ex | Ob | Ex | Ob | Ex | Ob | Ex | Ob | Ex |
| 8.75 | 0 | 0 | 0 | — | 0 | — | 0 | — | 0 | — | 60 | — | 0 | — |
| 17.5 | 0 | 0 | 10 | — | 0 | — | 0 | — | 0 | — | 65 | — | 0 | — |
| 35 | 0 | 0 | 20 | — | 0 | — | 0 | — | 0 | — | 65 | — | 0 | — |

TABLE 21-continued

Synergistic Activity of Herbicidal Compositions on Several Key Grass Weeds in Cereal Crops

| Application Rate (g/ha) | | | ALOMY | | APESV | | AVEFA | | LOLMG | | PESGL | | PHAMI | |
|---|---|---|---|---|---|---|---|---|---|---|---|---|---|---|
| Compound B Methyl | Fenoxaprop-p ethyl | Mefenpyr-diethyl | Ob | Ex | Ob | Ex | Ob | Ex | Ob | Ex | Ob | Ex | Ob | Ex |
| 70 | 0 | 0 | 40 | — | 0 | — | 0 | — | 0 | — | 70 | — | 0 | — |
| 0 | 23 | 6.27 | 50 | — | 70 | — | 0 | — | 0 | — | 85 | — | 0 | — |
| 8.75 | 23 | 6.27 | 90 | 50 | 90 | 70 | 95 | 0 | 75 | 0 | 100 | 94 | 70 | 0 |
| 17.5 | 23 | 6.27 | 90 | 55 | 90 | 70 | 95 | 0 | 70 | 0 | 100 | 95 | 70 | 0 |
| 35 | 23 | 6.27 | 90 | 60 | 90 | 70 | 95 | 0 | 70 | 0 | 100 | 95 | 70 | 0 |
| 70 | 23 | 6.27 | 90 | 70 | 90 | 70 | 95 | 0 | 60 | 0 | 100 | 96 | 60 | 0 |

TABLE 22

Synergistic Activity of Herbicidal Compositions on Several Key Grass Weeds in Cereal Crops

| Application Rate (g/ha) | | ALOMY | | APESV | | LOLMG | | PHAMI | |
|---|---|---|---|---|---|---|---|---|---|
| Compound B Methyl | Tralkoxydim | Ob | Ex | Ob | Ex | Ob | Ex | Ob | Ex |
| 8.75 | 0 | 0 | — | 0 | — | 0 | — | 0 | — |
| 17.5 | 0 | 10 | — | 0 | — | 0 | — | 0 | — |
| 35 | 0 | 20 | — | 0 | — | 0 | — | 0 | — |
| 70 | 0 | 40 | — | 0 | — | 0 | — | 0 | — |
| 0 | 50 | 70 | — | 75 | — | 50 | — | 30 | — |
| 8.75 | 50 | 85 | 70 | 85 | 75 | 55 | 50 | 65 | 30 |
| 17.5 | 50 | 85 | 73 | 85 | 75 | 55 | 50 | 65 | 30 |
| 35 | 50 | 85 | 76 | 85 | 75 | 60 | 50 | 65 | 30 |
| 70 | 50 | 70 | 82 | 75 | 75 | 65 | 50 | 50 | 30 |

TABLE 23

Synergistic Activity of Herbicidal Compositions on Several Key Broadleaf Weeds in Cereal Crops

| Application Rate (g/ha) | | CHEAL | | MATCH | | SINAR | | STEME | | VERPE | | VIOTR | |
|---|---|---|---|---|---|---|---|---|---|---|---|---|---|
| Compound A Methyl | Diflufenican | Ob | Ex | Ob | Ex | Ob | Ex | Ob | Ex | Ob | Ex | Ob | Ex |
| 17.5 | 0 | 90 | — | 15 | — | 70 | — | 78 | — | 45 | — | 55 | — |
| 35 | 0 | 90 | — | 68 | — | 80 | — | 90 | — | 58 | — | 63 | — |
| 70 | 0 | 95 | — | 65 | — | 85 | — | 100 | — | 70 | — | 75 | — |
| 0 | 15 | 0 | — | 5 | — | 0 | — | 3 | — | 38 | | 15 | — |
| 17.5 | 15 | 100 | 90 | 65 | 19 | 85 | 70 | 88 | 78 | 78 | 67 | 78 | 62 |
| 35 | 15 | 100 | 90 | 80 | 69 | 90 | 80 | 100 | 90 | 80 | 73 | 85 | 68 |
| 70 | 15 | 100 | 95 | 80 | 67 | 100 | 85 | 100 | 100 | 93 | 81 | 90 | 79 |

TABLE 24

Synergistic Activity of Herbicidal Compositions on Several Key Broadleaf Weeds in Cereal Crops

| Application Rate (g/ha) | | CHEAL | | MATCH | | SINAR | | STEME | | VERPE | | VIOTR | |
|---|---|---|---|---|---|---|---|---|---|---|---|---|---|
| Compound A Methyl | Liberator* | Ob | Ex | Ob | Ex | Ob | Ex | Ob | Ex | Ob | Ex | Ob | Ex |
| 17.5 | 0 | 90 | — | 20 | — | 80 | — | 75 | — | 40 | — | 40 | — |
| 35 | 0 | 90 | — | 85 | — | 85 | — | 95 | — | 55 | — | 50 | — |
| 70 | 0 | 95 | — | 80 | — | 85 | — | 100 | — | 80 | — | 60 | — |

TABLE 24-continued

Synergistic Activity of Herbicidal Compositions on Several Key Broadleaf Weeds in Cereal Crops

| Application Rate (g/ha) | | CHEAL | | MATCH | | SINAR | | STEME | | VERPE | | VIOTR | |
|---|---|---|---|---|---|---|---|---|---|---|---|---|---|
| Compound A Methyl | Liberator* | Ob | Ex | Ob | Ex | Ob | Ex | Ob | Ex | Ob | Ex | Ob | Ex |
| 0 | 75 | 30 | — | 10 | — | 30 | — | 20 | — | 10 | — | 10 | — |
| 17.5 | 75 | 100 | 93 | 70 | 28 | 85 | 86 | 100 | 80 | 65 | 46 | 70 | 46 |
| 35 | 75 | 100 | 93 | 95 | 87 | 85 | 90 | 100 | 96 | 75 | 60 | 75 | 55 |
| 70 | 75 | 100 | 97 | 95 | 82 | 95 | 90 | 100 | 100 | 90 | 82 | 85 | 64 |

*Liberator contains 100 g ai/l diflufenican and 400 g ai/l flufenacet

TABLE 25

Synergistic Activity of Herbicidal Compositions on Several Key Broadleaf Weeds in Cereal Crops

| Application Rate (g/ha) | | BRSNN | | POLPE | |
|---|---|---|---|---|---|
| Compound A Methyl | Pyroxsulam* | Ob | Ex | Ob | Ex |
| 8.75 | 0 | 50 | — | 50 | — |
| 17.5 | 0 | 50 | — | 50 | — |
| 35 | 0 | 50 | — | 65 | — |
| 70 | 0 | 50 | — | 70 | — |
| 0 | 7.5 | 75 | — | 75 | — |
| 8.75 | 7.5 | 100 | 88 | 95 | 88 |
| 17.5 | 7.5 | 100 | 88 | 95 | 88 |
| 35 | 7.5 | 100 | 88 | 95 | 91 |
| 70 | 7.5 | 100 | 88 | 95 | 93 |

*Pyroxsulam contains 30 g ai/l pyroxsulam and 90 g ai/l cloquintocet-mexyl

TABLE 26

Synergistic Activity of Herbicidal Compositions on Several Key Broadleaf Weeds in Cereal Crops

| Application Rate (g/ha) | | VERHE | | KCHSC | | SINAR | | VIOTR | | VERPE | |
|---|---|---|---|---|---|---|---|---|---|---|---|
| Compound A TEA | Picolinafen | Ob | Ex | Ob | Ex | Ob | Ex | Ob | Ex | Ob | Ex |
| 8.75 | 0 | 10 | — | 35 | — | 35 | — | 10 | — | 10 | — |
| 17.5 | 0 | 20 | — | 60 | — | 60 | — | 10 | — | 10 | — |
| 35 | 0 | 50 | — | 65 | — | 65 | — | 30 | — | 30 | — |
| 70 | 0 | 75 | — | 70 | — | 70 | — | 60 | — | 60 | — |
| 0 | 12.5 | 5 | — | 5 | — | 5 | — | 0 | — | 0 | — |
| 8.75 | 12.5 | 30 | 15 | 60 | 38 | 95 | 38 | 10 | 10 | 10 | 10 |
| 17.5 | 12.5 | 80 | 24 | 65 | 62 | 95 | 62 | 20 | 10 | 30 | 10 |
| 35 | 12.5 | 65 | 53 | 75 | 67 | 75 | 67 | 60 | 30 | 60 | 30 |
| 70 | 12.5 | 85 | 76 | 85 | 72 | 85 | 72 | 75 | 60 | 75 | 60 |

TABLE 27

Synergistic Activity of Herbicidal Compositions on Several Key Broadleaf Weeds in Cereal Crops

| Application Rate (g/ha) | | CIRAR | | VERPE | | VIOTR | |
|---|---|---|---|---|---|---|---|
| Compound A TEA | Amidosulfuron | Ob | Ex | Ob | Ex | Ob | Ex |
| 35 | 0 | 50 | — | 75 | — | 50 | — |
| 70 | 0 | 60 | — | 80 | — | 60 | — |
| 140 | 0 | 65 | — | 85 | — | 60 | — |

TABLE 27-continued

Synergistic Activity of Herbicidal Compositions on Several Key Broadleaf Weeds in Cereal Crops

| Application Rate (g/ha) | | CIRAR | | VERPE | | VIOTR | |
|---|---|---|---|---|---|---|---|
| Compound A TEA | Amidosulfuron | Ob | Ex | Ob | Ex | Ob | Ex |
| 0 | 10 | 20 | — | 5 | — | 5 | — |
| 35 | 10 | 75 | 60 | 85 | 76 | 50 | 53 |
| 70 | 10 | 85 | 68 | 85 | 81 | 70 | 62 |
| 140 | 10 | 90 | 72 | 87 | 86 | 70 | 62 |

TABLE 28

Synergistic Activity of Herbicidal Compositions on Several Key Broadleaf Weeds in Cereal Crops

| Application Rate (g/ha) | | VERPE | |
|---|---|---|---|
| Compound A TEA | Chlorsulfuron | Ob | Ex |
| 35 | 0 | 75 | — |
| 70 | 0 | 80 | — |
| 140 | 0 | 85 | — |
| 0 | 2.2 | 5 | — |
| 35 | 2.2 | 87 | 76 |

TABLE 28-continued

Synergistic Activity of Herbicidal Compositions on Several Key Broadleaf Weeds in Cereal Crops

| Application Rate (g/ha) | | VERPE | |
|---|---|---|---|
| Compound A TEA | Chlorsulfuron | Ob | Ex |
| 70 | 2.2 | 95 | 81 |
| 140 | 2.2 | 95 | 86 |

TABLE 29

Synergistic Activity of Herbicidal Compositions on Several Key Broadleaf Weeds in Cereal Crops

| Application Rate (g/ha) | | CIRAR | | VERPE | | VIOTR | |
|---|---|---|---|---|---|---|---|
| Compound A TEA | Florasulam | Ob | Ex | Ob | Ex | Ob | Ex |
| 35 | 0 | 50 | — | 75 | — | 50 | — |
| 70 | 0 | 60 | — | 80 | — | 60 | — |
| 140 | 0 | 65 | — | 85 | — | 60 | — |
| 0 | 1.25 | 20 | — | 5 | — | 10 | — |
| 35 | 1.25 | 90 | 60 | 95 | 76 | 70 | 55 |
| 70 | 1.25 | 95 | 68 | 95 | 81 | 65 | 64 |
| 140 | 1.25 | 95 | 72 | 97 | 86 | 70 | 64 |

TABLE 30

Synergistic Activity of Herbicidal Compositions on Several Key Broadleaf Weeds in Cereal Crops

| Application Rate (g/ha) | | VERPE | | CIRAR | | VERPE | | VIOTR | |
|---|---|---|---|---|---|---|---|---|---|
| Compound A TEA | Flupyr-sulfuron | Ob | Ex | Ob | Ex | Ob | Ex | Ob | Ex |
| 35 | 0 | 60 | — | 50 | — | 75 | — | 50 | — |
| 70 | 0 | 60 | — | 60 | — | 80 | — | 60 | — |
| 140 | 0 | 60 | — | 65 | — | 85 | — | 60 | — |
| 0 | 5 | 0 | — | 20 | — | 0 | — | 0 | — |
| 35 | 5 | 70 | 60 | 80 | 60 | 80 | 75 | 50 | 50 |
| 70 | 5 | 75 | 60 | 90 | 68 | 97 | 80 | 65 | 60 |
| 140 | 5 | 75 | 60 | 85 | 72 | 90 | 85 | 65 | 60 |

TABLE 31

Synergistic Activity of Herbicidal Compositions on Several Key Broadleaf Weeds in Cereal Crops

| Application Rate (g/ha) | | CIRAR | |
|---|---|---|---|
| Compound A TEA | Iodosulfuron | Ob | Ex |
| 35 | 0 | 50 | — |
| 70 | 0 | 60 | — |
| 140 | 0 | 65 | — |
| 0 | 3.75 | 50 | — |
| 35 | 3.75 | 90 | 75 |
| 70 | 3.75 | 93 | 80 |
| 140 | 3.75 | 95 | 83 |

TABLE 32

Synergistic Activity of Herbicidal Compositions on Several Key Broadleaf Weeds in Cereal Crops

| Application Rate (g/ha) | | VERPE | | CIRAR | | VIOTR | | STEME | | MATCH | |
|---|---|---|---|---|---|---|---|---|---|---|---|
| Compound A TEA | Mesosulfuron | Ob | Ex | Ob | Ex | Ob | Ex | Ob | Ex | Ob | Ex |
| 35 | 0 | 60 | — | 50 | — | 50 | — | 55 | — | 60 | — |
| 70 | 0 | 60 | — | 60 | — | 60 | — | 60 | — | 60 | — |
| 140 | 0 | 60 | — | 65 | — | 60 | — | 65 | — | 65 | — |
| 0 | 3.75 | 0 | — | 20 | — | 0 | — | 0 | — | 5 | — |
| 35 | 3.75 | 75 | 60 | 95 | 60 | 65 | 50 | 70 | 55 | 60 | 62 |
| 70 | 3.75 | 75 | 60 | 95 | 68 | 65 | 60 | 70 | 60 | 80 | 62 |
| 140 | 3.75 | 75 | 60 | 95 | 72 | 70 | 60 | 75 | 65 | 85 | 67 |

TABLE 33

Synergistic Activity of Herbicidal Compositions on Several Key Broadleaf Weeds in Cereal Crops

| Application Rate (g/ha) | | CIRAR | |
|---|---|---|---|
| Compound A TEA | Metsulfuron | Ob | Ex |
| 35 | 0 | 50 | — |
| 70 | 0 | 60 | — |
| 140 | 0 | 65 | — |
| 0 | 3.75 | 20 | — |
| 35 | 3.75 | 80 | 60 |

TABLE 33-continued

Synergistic Activity of Herbicidal Compositions on Several Key Broadleaf Weeds in Cereal Crops

| Application Rate (g/ha) Compound A | | CIRAR | |
|---|---|---|---|
| TEA | Metsulfuron | Ob | Ex |
| 70 | 3.75 | 85 | 68 |
| 140 | 3.75 | 85 | 72 |

TABLE 34

Synergistic Activity of Herbicidal Compositions on Several Key Broadleaf Weeds in Cereal Crops

| Application Rate (g/ha) Compound A | Propoxycarbazone- | VERPE | | MATCH | |
|---|---|---|---|---|---|
| TEA | sodium | Ob | Ex | Ob | Ex |
| 35 | 0 | 75 | — | 60 | — |
| 70 | 0 | 80 | — | 60 | — |
| 140 | 0 | 85 | — | 65 | — |
| 0 | 15 | 5 | — | 50 | — |
| 35 | 15 | 75 | 76 | 80 | 80 |
| 70 | 15 | 90 | 81 | 87 | 80 |
| 140 | 15 | 95 | 86 | 87 | 83 |

TABLE 35

Synergistic Activity of Herbicidal Compositions on Several Key Broadleaf Weeds in Cereal Crops

| Application Rate (g/ha) Compound A | | CIRAR | |
|---|---|---|---|
| TEA | Pyroxsulam* | Ob | Ex |
| 35 | 0 | 50 | — |
| 70 | 0 | 60 | — |
| 140 | 0 | 65 | — |
| 0 | 3.75 | 20 | — |
| 35 | 3.75 | 90 | 60 |
| 70 | 3.75 | 95 | 68 |
| 140 | 3.75 | 95 | 72 |

*Pyroxsulam contains 30 g ai/l pyroxsulam and 90 g ai/l cloquintocet-mexyl

TABLE 36

Synergistic Activity of Herbicidal Compositions on Several Key Broadleaf Weeds in Cereal Crops

| Application Rate (g/ha) Compound A | | CIRAR | | VERPE | |
|---|---|---|---|---|---|
| TEA | Sulfosulfuron | Ob | Ex | Ob | Ex |
| 35 | 0 | 50 | — | 75 | — |
| 70 | 0 | 60 | — | 80 | — |
| 140 | 0 | 65 | — | 85 | — |
| 0 | 8.75 | 10 | — | 30 | — |
| 35 | 8.75 | 75 | 55 | 80 | 83 |
| 70 | 8.75 | 93 | 64 | 97 | 86 |
| 140 | 8.75 | 80 | 69 | 97 | 90 |

TABLE 37

Synergistic Activity of Herbicidal Compositions on Several Key Broadleaf Weeds in Cereal Crops

| Application Rate (g/ha) Compound A | | CIRAR | |
|---|---|---|---|
| TEA | Thifensulfuron | Ob | Ex |
| 35 | 0 | 50 | — |
| 70 | 0 | 60 | — |
| 140 | 0 | 65 | — |
| 0 | 3.75 | 20 | — |
| 35 | 3.75 | 80 | 60 |
| 70 | 3.75 | 90 | 68 |
| 140 | 3.75 | 85 | 72 |

TABLE 38

Synergistic Activity of Herbicidal Compositions on Several Key Broadleaf Weeds in Cereal Crops

| Application Rate (g/ha) Compound A | | CIRAR | |
|---|---|---|---|
| TEA | Tribenuron | Ob | Ex |
| 35 | 0 | 50 | — |
| 70 | 0 | 60 | — |
| 140 | 0 | 65 | — |
| 0 | 3.75 | 20 | — |
| 35 | 3.75 | 93 | 60 |
| 70 | 3.75 | 95 | 68 |
| 140 | 3.75 | 95 | 72 |

TABLE 39

Synergistic Activity of Herbicidal Compositions on Several Key Broadleaf Weeds in Cereal Crops

| Application Rate (g/ha) Compound A | | STEME | | MATCH | |
|---|---|---|---|---|---|
| TEA | Imazamethabenz | Ob | Ex | Ob | Ex |
| 35 | 0 | 55 | — | 60 | — |
| 70 | 0 | 60 | — | 60 | — |
| 140 | 0 | 65 | — | 65 | — |
| 0 | 125 | 10 | — | 0 | — |
| 35 | 125 | 75 | 60 | 60 | 60 |
| 70 | 125 | 100 | 64 | 80 | 60 |
| 140 | 125 | 100 | 69 | 80 | 65 |

TABLE 40

Synergistic Activity of Herbicidal Compositions on Several Key Broadleaf Weeds in Cereal Crops

| Application Rate (g/ha) | | BRSNI | | GERDI | | POLCO | | STEME | | VERPE | | VIOTR | |
|---|---|---|---|---|---|---|---|---|---|---|---|---|---|
| Compound A TEA | Beflubutamid | Ob | Ex | Ob | Ex | Ob | Ex | Ob | Ex | Ob | Ex | Ob | Ex |
| 8.75 | 0 | 70 | — | 50 | — | 90 | — | 80 | — | 48 | — | 30 | — |
| 17.5 | 0 | 91 | — | 55 | — | 93 | — | 85 | — | 68 | — | 40 | — |
| 35 | 0 | 98 | — | 65 | — | 98 | — | 88 | — | 79 | — | 47 | — |
| 0 | 35 | 30 | — | 0 | — | 10 | — | 10 | — | 15 | — | 15 | — |
| 0 | 70 | 30 | — | 0 | — | 20 | — | 10 | — | 23 | — | 23 | — |
| 8.75 | 35 | 85 | 79 | 60 | 50 | 100 | 91 | 95 | 82 | 61 | 56 | 68 | 41 |
| 17.5 | 35 | 100 | 94 | 60 | 55 | 100 | 93 | 100 | 87 | 79 | 73 | 66 | 49 |
| 35 | 35 | 100 | 98 | 75 | 65 | 100 | 98 | 100 | 89 | 84 | 82 | 76 | 55 |
| 8.75 | 70 | 100 | 79 | 70 | 50 | 100 | 92 | 100 | 82 | 61 | 60 | 49 | 46 |
| 17.5 | 70 | 100 | 94 | 75 | 55 | 100 | 94 | 100 | 87 | 83 | 76 | 74 | 54 |
| 35 | 70 | 100 | 98 | 80 | 65 | 100 | 98 | 100 | 89 | 89 | 84 | 80 | 59 |

TABLE 41

Synergistic Activity of Herbicidal Compositions on Several Key Broadleaf Weeds in Cereal Crops

| Application Rate (g/ha) Compound A TEA | Bentazone | BRSNI Ob | BRSNI Ex | POLCO Ob | POLCO Ex | VERPE Ob | VERPE Ex | VIOTR Ob | VIOTR Ex |
|---|---|---|---|---|---|---|---|---|---|
| 8.75 | 0 | 70 | — | 90 | — | 48 | — | 30 | — |
| 17.5 | 0 | 91 | — | 93 | — | 68 | — | 40 | — |
| 35 | 0 | 98 | — | 98 | — | 79 | — | 47 | — |
| 70 | 0 | 99 | — | 99 | — | 88 | — | 60 | — |
| 0 | 120 | 50 | — | 0 | — | 0 | — | 0 | — |
| 8.75 | 120 | 100 | 85 | 100 | 90 | 65 | 48 | 60 | 30 |
| 17.5 | 120 | 100 | 96 | 97 | 93 | 70 | 68 | 65 | 40 |
| 35 | 120 | 100 | 99 | 100 | 98 | 87 | 79 | 70 | 47 |
| 70 | 120 | 100 | 99 | 100 | 99 | 93 | 88 | 75 | 60 |

TABLE 42

Synergistic Activity of Herbicidal Compositions on Several Key Broadleaf Weeds in Cereal Crops

| Application Rate (g/ha) Compound A TEA | Bromoxynil | BRSNI Ob | BRSNI Ex | MATCH Ob | MATCH Ex | STEME Ob | STEME Ex |
|---|---|---|---|---|---|---|---|
| 8.75 | 0 | 70 | — | 71 | — | 80 | — |
| 17.5 | 0 | 91 | — | 76 | — | 85 | — |
| 35 | 0 | 98 | — | 84 | — | 88 | — |
| 70 | 0 | 99 | — | 94 | — | 93 | — |
| 0 | 70 | 50 | — | 0 | — | 0 | — |
| 17.5 | 70 | 100 | 96 | 85 | 76 | 97 | 85 |
| 35 | 70 | 100 | 99 | 93 | 84 | 97 | 88 |
| 70 | 70 | 100 | 99 | 95 | 94 | 100 | 93 |

TABLE 43

Synergistic Activity of Herbicidal Compositions on Several Key Broadleaf Weeds in Cereal Crops

| Application Rate (g/ha) Compound A TEA | Chlormequat | BRSNI Ob | BRSNI Ex | GERDI Ob | GERDI Ex | KCHSC Ob | KCHSC Ex | MATCH Ob | MATCH Ex | POLCO Ob | POLCO Ex | STEME Ob | STEME Ex |
|---|---|---|---|---|---|---|---|---|---|---|---|---|---|
| 8.75 | 0 | 70 | — | 50 | — | 65 | — | 71 | — | 90 | — | 80 | — |
| 17.5 | 0 | 91 | — | 55 | — | 77 | — | 76 | — | 93 | — | 85 | — |
| 35 | 0 | 98 | — | 65 | — | 92 | — | 84 | — | 98 | — | 88 | — |
| 70 | 0 | 99 | — | 78 | — | 99 | — | 94 | — | 99 | — | 93 | — |
| 0 | 155 | 0 | — | 0 | — | 0 | — | 0 | — | 10 | — | 0 | — |
| 8.75 | 155 | 100 | 70 | 75 | 50 | 70 | 65 | 93 | 71 | 100 | 91 | 100 | 80 |
| 17.5 | 155 | 100 | 91 | 75 | 55 | 100 | 77 | 100 | 76 | 100 | 93 | 100 | 85 |
| 35 | 155 | 100 | 98 | 60 | 65 | 100 | 92 | 100 | 84 | 100 | 98 | 100 | 88 |
| 70 | 155 | 100 | 99 | 50 | 78 | 100 | 99 | 100 | 94 | 100 | 99 | 100 | 93 |

TABLE 44

Synergistic Activity of Herbicidal Compositions on Several Key Broadleaf Weeds in Cereal Crops

| Application Rate (g/ha) | | BRSNI | | KCHSC | |
|---|---|---|---|---|---|
| Compound A TEA | Chlorotoluron | Ob | Ex | Ob | Ex |
| 8.75 | 0 | 70 | — | 65 | — |
| 17.5 | 0 | 91 | — | 77 | — |
| 35 | 0 | 98 | — | 92 | — |
| 70 | 0 | 99 | — | 99 | — |
| 0 | 450 | 50 | — | 50 | — |
| 8.75 | 450 | 100 | 85 | 100 | 83 |
| 17.5 | 450 | 100 | 96 | 100 | 89 |
| 35 | 450 | 100 | 99 | 97 | 96 |

TABLE 45

Synergistic Activity of Herbicidal Compositions on Several Key Broadleaf Weeds in Cereal Crops

| Application Rate (g/ha) | | MATCH | | POLCO | | STEME | |
|---|---|---|---|---|---|---|---|
| Compound A TEA | Indol-3-acetic acid | Ob | Ex | Ob | Ex | Ob | Ex |
| 8.75 | 0 | 71 | — | 90 | — | 80 | — |
| 17.5 | 0 | 76 | — | 93 | — | 85 | — |
| 35 | 0 | 84 | — | 98 | — | 88 | — |
| 70 | 0 | 94 | — | 99 | — | 93 | — |
| 0 | 140 | 0 | — | 0 | — | 0 | — |
| 8.75 | 140 | 80 | 71 | 100 | 90 | 85 | 80 |
| 17.5 | 140 | 90 | 76 | 100 | 93 | 97 | 85 |
| 35 | 140 | 93 | 84 | 100 | 98 | 100 | 88 |
| 70 | 140 | 95 | 94 | 100 | 99 | 100 | 93 |

TABLE 46

Synergistic Activity of Herbicidal Compositions on Several Key Broadleaf Weeds in Cereal Crops

| Application Rate (g/ha) | | BRSNI | | STEME | |
|---|---|---|---|---|---|
| Compound A TEA | Indol-3-butyric acid | Ob | Ex | Ob | Ex |
| 8.75 | 0 | 70 | — | 80 | — |
| 17.5 | 0 | 91 | — | 85 | — |
| 35 | 0 | 98 | — | 88 | — |
| 70 | 0 | 99 | — | 93 | — |
| 0 | 140 | 0 | — | 0 | — |
| 8.75 | 140 | 80 | 70 | 80 | 80 |
| 17.5 | 140 | 93 | 91 | 90 | 85 |
| 35 | 140 | 100 | 98 | 100 | 88 |
| 70 | 140 | 100 | 99 | 100 | 93 |

TABLE 47

Synergistic Activity of Herbicidal Compositions on Several Key Broadleaf Weeds in Cereal Crops

| Application Rate (g/ha) | | BRSNI | | KCHSC | | SASKR | | VIOTR | |
|---|---|---|---|---|---|---|---|---|---|
| Compound A TEA | Isoproturon | Ob | Ex | Ob | Ex | Ob | Ex | Ob | Ex |
| 8.75 | 0 | 70 | — | 65 | — | 80 | — | 30 | — |
| 17.5 | 0 | 91 | — | 77 | — | 84 | — | 40 | — |

TABLE 47-continued

Synergistic Activity of Herbicidal Compositions on Several Key Broadleaf Weeds in Cereal Crops

| Application Rate (g/ha) | | BRSNI | | KCHSC | | SASKR | | VIOTR | |
|---|---|---|---|---|---|---|---|---|---|
| Compound A TEA | Isoproturon | Ob | Ex | Ob | Ex | Ob | Ex | Ob | Ex |
| 35 | 0 | 98 | — | 92 | — | 87 | — | 47 | — |
| 70 | 0 | 99 | — | 99 | — | 93 | — | 60 | — |
| 0 | 300 | 40 | — | 50 | — | 33 | — | 0 | — |
| 8.75 | 300 | 93 | 82 | 100 | 83 | 89 | 87 | 30 | 30 |
| 17.5 | 300 | 100 | 95 | 100 | 89 | 90 | 89 | 45 | 40 |
| 35 | 300 | 100 | 99 | 100 | 96 | 97 | 91 | 60 | 47 |
| 70 | 300 | 100 | 99 | 97 | 99 | 95 | 95 | 73 | 60 |

TABLE 48

Synergistic Activity of Herbicidal Compositions on Several Key Broadleaf Weeds in Cereal Crops

| Application Rate (g/ha) | | VERPE | | VIOTR | |
|---|---|---|---|---|---|
| Compound A TEA | Isoxaben | Ob | Ex | Ob | Ex |
| 8.75 | 0 | 48 | — | 30 | — |
| 17.5 | 0 | 68 | — | 40 | — |
| 35 | 0 | 79 | — | 47 | — |
| 70 | 0 | 88 | — | 60 | — |
| 0 | 31.25 | 0 | — | 3 | — |
| 8.75 | 31.25 | 61 | 48 | 48 | 32 |
| 17.5 | 31.25 | 71 | 68 | 50 | 42 |
| 35 | 31.25 | 84 | 79 | 61 | 48 |
| 70 | 31.25 | 95 | 88 | 70 | 61 |

TABLE 49

Synergistic Activity of Herbicidal Compositions on Several Key Broadleaf Weeds in Cereal Crops

| Application Rate (g/ha) | | BRSNI | | VERPE | | VIOTR | |
|---|---|---|---|---|---|---|---|
| Compound A TEA | Metribuzin | Ob | Ex | Ob | Ex | Ob | Ex |
| 8.75 | 0 | 70 | — | 48 | — | 30 | — |
| 17.5 | 0 | 91 | — | 68 | — | 40 | — |
| 35 | 0 | 98 | — | 79 | — | 47 | — |
| 70 | 0 | 99 | — | 88 | — | 60 | — |
| 0 | 50 | 50 | — | 10 | — | 20 | — |
| 8.75 | 50 | 100 | 85 | 60 | 53 | 60 | 44 |
| 17.5 | 50 | 100 | 96 | 90 | 72 | 80 | 52 |
| 35 | 50 | 100 | 99 | 90 | 81 | 80 | 58 |
| 70 | 50 | 100 | 99 | 95 | 89 | 85 | 68 |

TABLE 50

Synergistic Activity of Herbicidal Compositions on Several Key Broadleaf Weeds in Cereal Crops

| Application Rate (g/ha) | | BRSNI | | MATCH | | SASKR | | STEME | |
|---|---|---|---|---|---|---|---|---|---|
| Compound A TEA | Prosulfocarb | Ob | Ex | Ob | Ex | Ob | Ex | Ob | Ex |
| 8.75 | 0 | 70 | — | 71 | — | 80 | — | 80 | — |
| 17.5 | 0 | 91 | — | 76 | — | 84 | — | 85 | — |
| 35 | 0 | 98 | — | 84 | — | 87 | — | 88 | — |

TABLE 50-continued

Synergistic Activity of Herbicidal Compositions on Several Key Broadleaf Weeds in Cereal Crops

| Application Rate (g/ha) | | | | | | | | | |
|---|---|---|---|---|---|---|---|---|---|
| Compound | | BRSNI | | MATCH | | SASKR | | STEME | |
| A TEA | Prosulfocarb | Ob | Ex | Ob | Ex | Ob | Ex | Ob | Ex |
| 70 | 0 | 99 | — | 94 | — | 93 | — | 93 | — |
| 0 | 500 | 0 | — | 0 | — | 0 | — | 0 | — |
| 8.75 | 500 | 97 | 70 | 95 | 71 | 85 | 80 | 85 | 80 |
| 17.5 | 500 | 100 | 91 | 95 | 76 | 90 | 84 | 85 | 85 |
| 35 | 500 | 100 | 98 | 97 | 84 | 90 | 87 | 100 | 88 |
| 70 | 500 | 100 | 99 | 95 | 94 | 90 | 93 | 100 | 93 |

TABLE 51

Synergistic Activity of Herbicidal Compositions on Several Key Broadleaf Weeds in Cereal Crops

| Application Rate (g/ha) | | | | | |
|---|---|---|---|---|---|
| Compound A | | KCHSC | | STEME | |
| TEA | Quinclorac | Ob | Ex | Ob | Ex |
| 8.75 | 0 | 65 | — | 80 | — |
| 17.5 | 0 | 77 | — | 85 | — |
| 35 | 0 | 92 | — | 88 | — |
| 70 | 0 | 99 | — | 93 | — |
| 0 | 140 | 0 | — | 0 | — |
| 8.75 | 140 | 65 | 65 | 87 | 80 |
| 17.5 | 140 | 90 | 77 | 90 | 85 |
| 35 | 140 | 100 | 92 | 100 | 88 |
| 70 | 140 | 100 | 99 | 100 | 93 |

TABLE 52

Synergistic Activity of Herbicidal Compositions on Several Key Broadleaf Weeds in Cereal Crops

| Application Rate (g/ha) | | | | | | | |
|---|---|---|---|---|---|---|---|
| Compound A | | GERDI | | MATCH | | BRSNI | |
| TEA | Aminopyralid | Ob | Ex | Ob | Ex | Ob | Ex |
| 8.75 | 0 | 38 | — | 59 | — | 83 | — |
| 17.5 | 0 | 50 | — | 76 | — | 93 | — |
| 35 | 0 | 80 | — | 88 | — | 97 | — |
| 70 | 0 | 85 | — | 93 | — | 100 | — |
| 0 | 2.5 | 0 | — | 10 | — | 0 | — |
| 8.75 | 2.5 | 65 | 38 | 90 | 63 | 93 | 83 |
| 17.5 | 2.5 | 60 | 50 | 95 | 78 | 97 | 93 |

TABLE 53

Synergistic Activity of Herbicidal Compositions on Several Key Broadleaf Weeds in Cereal Crops

| Application Rate (g/ha) | | | | | | | |
|---|---|---|---|---|---|---|---|
| Compound A | | MATCH | | VERPE | | BRSNI | |
| TEA | Dicamba | Ob | Ex | Ob | Ex | Ob | Ex |
| 8.75 | 0 | 59 | — | 59 | — | 83 | — |
| 17.5 | 0 | 76 | — | 69 | — | 93 | — |
| 35 | 0 | 88 | — | 86 | — | 97 | — |
| 70 | 0 | 93 | — | 85 | — | 100 | — |
| 0 | 35 | 30 | — | 10 | — | 50 | — |

TABLE 53-continued

Synergistic Activity of Herbicidal Compositions on Several Key Broadleaf Weeds in Cereal Crops

| Application Rate (g/ha) | | | | | | | |
|---|---|---|---|---|---|---|---|
| Compound A | | MATCH | | VERPE | | BRSNI | |
| TEA | Dicamba | Ob | Ex | Ob | Ex | Ob | Ex |
| 8.75 | 35 | 87 | 71 | 80 | 63 | 95 | 92 |
| 17.5 | 35 | 90 | 83 | 85 | 72 | 100 | 97 |

TABLE 54

Synergistic Activity of Herbicidal Compositions on Several Key Broadleaf Weeds in Cereal Crops

| Application Rate (g/ha) | | | | | |
|---|---|---|---|---|---|
| Compound A | | MATCH | | VERPE | |
| TEA | Dichlorprop | Ob | Ex | Ob | Ex |
| 8.75 | 0 | 59 | — | 59 | — |
| 17.5 | 0 | 76 | — | 69 | — |
| 35 | 0 | 88 | — | 86 | — |
| 70 | 0 | 93 | — | 85 | — |
| 0 | 140 | 10 | — | 20 | — |
| 8.75 | 140 | 87 | 63 | 80 | 67 |
| 17.5 | 140 | 90 | 78 | 85 | 75 |

TABLE 55

Synergistic Activity of Herbicidal Compositions on Several Key Broadleaf Weeds in Cereal Crops

| Application Rate (g/ha) | | | | | | | | | | | |
|---|---|---|---|---|---|---|---|---|---|---|---|
| Compound | | POLCO | | VERPE | | VIOTR | | STEME | | POLPE | |
| A TEA | MCPA | Ob | Ex | Ob | Ex | Ob | Ex | Ob | Ex | Ob | Ex |
| 8.75 | 0 | 76 | — | 59 | — | 34 | — | 76 | — | 30 | — |
| 17.5 | 0 | 88 | — | 69 | — | 44 | — | 85 | — | 41 | — |
| 35 | 0 | 96 | — | 86 | — | 58 | — | 91 | — | 68 | — |
| 0 | 70 | 7 | — | 10 | — | 17 | — | 7 | — | 23 | — |
| 8.75 | 70 | 83 | 78 | 73 | 63 | 53 | 45 | 89 | 78 | 45 | 46 |
| 17.5 | 70 | 95 | 88 | 80 | 72 | 60 | 53 | 94 | 86 | 65 | 55 |
| 35 | 70 | 100 | 96 | 87 | 87 | 72 | 65 | 98 | 92 | 84 | 75 |

TABLE 56

Synergistic Activity of Herbicidal Compositions on Several Key Broadleaf Weeds in Cereal Crops

| Application Rate (g/ha) | | | | | |
|---|---|---|---|---|---|
| Compound | | BRSNN | | MATCH | |
| B Methyl | Pyroxsulam* | Ob | Ex | Ob | Ex |
| 8.75 | 0 | 20 | — | 10 | — |
| 17.5 | 0 | 35 | — | 10 | — |
| 35 | 0 | 50 | — | 40 | — |
| 70 | 0 | 55 | — | 45 | — |
| 0 | 3.75 | 90 | — | 65 | — |
| 8.75 | 3.75 | 99 | 92 | 90 | 69 |
| 17.5 | 3.75 | 99 | 94 | 85 | 69 |
| 35 | 3.75 | 99 | 95 | 85 | 79 |
| 70 | 3.75 | 100 | 96 | 85 | 81 |

*Pyroxsulam contains 30 g ai/l pyroxsulam and 90 g ai/l cloquintocet-mexyl

TABLE 57

Synergistic Activity of Herbicidal Compositions on Several Key Broadleaf Weeds in Cereal Crops

| Application Rate (g/ha) | | MATCH | | SASKR | | KCHSC | | VERPE | | VIOTR | |
|---|---|---|---|---|---|---|---|---|---|---|---|
| Compound A K-salt | Aminopyralid | Ob | Ex | Ob | Ex | Ob | Ex | Ob | Ex | Ob | Ex |
| 8.75 | 0 | 50 | — | 63 | — | 67 | — | 73 | — | 20 | — |
| 17.5 | 0 | 62 | — | 67 | — | 77 | — | 78 | — | 48 | — |
| 35 | 0 | 57 | — | 73 | — | 90 | — | 83 | — | 42 | — |
| 0 | 2.5 | 8 | — | 18 | — | 0 | — | 0 | — | 27 | — |
| 8.75 | 2.5 | 72 | 54 | 75 | 70 | 75 | 67 | 82 | 73 | 57 | 41 |
| 17.5 | 2.5 | 80 | 65 | 85 | 73 | 88 | 77 | 87 | 78 | 70 | 62 |
| 35 | 2.5 | 85 | 60 | 90 | 78 | 95 | 90 | 85 | 83 | 72 | 57 |

TABLE 58

Synergistic Activity of Herbicidal Compositions on Several Key Broadleaf Weeds in Cereal Crops

| Application Rate (g/ha) | | MATCH | | SASKR | | VERPE | | VIOTR | |
|---|---|---|---|---|---|---|---|---|---|
| Compound A K-salt | Picolinafen | Ob | Ex | Ob | Ex | Ob | Ex | Ob | Ex |
| 8.75 | 0 | 50 | — | 63 | — | 73 | — | 20 | — |
| 17.5 | 0 | 62 | — | 67 | — | 78 | — | 48 | — |
| 35 | 0 | 57 | — | 73 | — | 83 | — | 42 | — |
| 0 | 15 | 10 | — | 60 | — | 43 | — | 78 | — |
| 8.75 | 15 | 90 | 55 | 83 | 85 | 95 | 85 | 95 | 83 |
| 17.5 | 15 | 83 | 66 | 90 | 87 | 95 | 88 | 88 | 89 |
| 35 | 15 | 87 | 61 | 95 | 89 | 98 | 91 | 98 | 87 |

TABLE 59

Synergistic Activity of Herbicidal Compositions on Several Key Broadleaf Weeds in Cereal Crops

| Application Rate (g/ha) | | MATCH | | VERPE | | VIOTR | |
|---|---|---|---|---|---|---|---|
| Compound A K-salt | Aminopyralid + Picolinafen | Ob | Ex | Ob | Ex | Ob | Ex |
| 8.75 | 0 | 50 | — | 73 | — | 20 | — |
| 17.5 | 0 | 62 | — | 78 | — | 48 | — |
| 35 | 0 | 57 | — | 83 | — | 42 | — |
| 0 | 2.5 + 15 | 25 | — | 38 | — | 72 | — |
| 8.75 | 2.5 + 15 | 70 | 59 | 98 | 85 | 100 | 87 |
| 17.5 | 2.5 + 15 | 73 | 68 | 100 | 88 | 96 | 92 |
| 35 | 2.5 + 15 | 90 | 64 | 99 | 91 | 100 | 91 |

TABLE 60

Synergistic Activity of Herbicidal Compositions on Several Key Broadleaf Weeds in Cereal Crops

| Application Rate (g/ha) | | MATCH | | KCHSC | | VERPE | | VIOTR | |
|---|---|---|---|---|---|---|---|---|---|
| Compound A K-salt | Diflufenican | Ob | Ex | Ob | Ex | Ob | Ex | Ob | Ex |
| 8.75 | 0 | 50 | — | 67 | — | 73 | — | 20 | — |
| 17.5 | 0 | 62 | — | 77 | — | 78 | — | 48 | — |
| 35 | 0 | 57 | — | 90 | — | 83 | — | 42 | — |
| 0 | 12.5 | 7 | — | 12 | — | 7 | — | 35 | — |
| 8.75 | 12.5 | 82 | 53 | 80 | 71 | 88 | 75 | 58 | 48 |

TABLE 60-continued

Synergistic Activity of Herbicidal Compositions on Several Key Broadleaf Weeds in Cereal Crops

| Application Rate (g/ha) | | MATCH | | KCHSC | | VERPE | | VIOTR | |
|---|---|---|---|---|---|---|---|---|---|
| Compound A K-salt | Diflufenican | Ob | Ex | Ob | Ex | Ob | Ex | Ob | Ex |
| 17.5 | 12.5 | 85 | 64 | 82 | 79 | 90 | 80 | 80 | 66 |
| 35 | 12.5 | 87 | 60 | 90 | 91 | 93 | 84 | 82 | 62 |

TABLE 61

Synergistic Activity of Herbicidal Compositions on Several Key Broadleaf Weeds in Cereal Crops

| Application Rate (g/ha) | | MATCH | | KCHSC | | VERPE | | VIOTR | |
|---|---|---|---|---|---|---|---|---|---|
| Compound A K-salt | Aminopyralid + Diflufenican | Ob | Ex | Ob | Ex | Ob | Ex | Ob | Ex |
| 8.75 | 0 | 50 | — | 67 | — | 73 | — | 20 | — |
| 17.5 | 0 | 62 | — | 77 | — | 78 | — | 48 | — |
| 35 | 0 | 57 | — | 90 | — | 83 | — | 42 | — |
| 0 | 2.5 + 12.5 | 23 | — | 27 | — | 35 | — | 63 | — |
| 8.75 | 2.5 + 12.5 | 80 | 57 | 82 | 71 | 95 | 75 | 86 | 62 |
| 17.5 | 2.5 + 12.5 | 80 | 67 | 85 | 79 | 93 | 80 | 90 | 75 |
| 35 | 2.5 + 12.5 | 83 | 63 | 93 | 91 | 93 | 84 | 93 | 72 |

TABLE 62

Synergistic Activity of Herbicidal Compositions on Several Key Broadleaf Weeds in Cereal Crops

| Application Rate (g/ha) | | MATCH | | VERPE | | VIOTR | |
|---|---|---|---|---|---|---|---|
| Compound A K-salt | Florasulam | Ob | Ex | Ob | Ex | Ob | Ex |
| 8.75 | 0 | 50 | — | 73 | — | 20 | — |
| 17.5 | 0 | 62 | — | 78 | — | 48 | — |
| 35 | 0 | 57 | — | 83 | — | 42 | — |
| 0 | 1.3 | 83 | — | 28 | — | 53 | — |
| 8.75 | 1.3 | 95 | 92 | 80 | 81 | 77 | 63 |
| 17.5 | 1.3 | 98 | 94 | 91 | 85 | 80 | 76 |
| 35 | 1.3 | 98 | 93 | 90 | 88 | 80 | 73 |

TABLE 63

Synergistic Activity of Herbicidal Compositions on Several Key Broadleaf Weeds in Cereal Crops

| Application Rate (g/ha) | | | | | | | |
|---|---|---|---|---|---|---|---|
| Compound | | SASKR | | KCHSC | | VIOTR | |
| A K-salt | Glyphosate | Ob | Ex | Ob | Ex | Ob | Ex |
| 8.75 | 0 | 63 | — | 67 | — | 20 | — |
| 17.5 | 0 | 67 | — | 77 | — | 48 | — |
| 35 | 0 | 73 | — | 90 | — | 42 | — |
| 0 | 52.5 | 0 | — | 0 | — | 52 | — |
| 8.75 | 52.5 | 83 | 63 | 68 | 67 | 75 | 61 |
| 17.5 | 52.5 | 87 | 67 | 83 | 77 | 77 | 75 |
| 35 | 52.5 | 87 | 73 | 87 | 90 | 83 | 72 |

TABLE 64

Synergistic Activity of Herbicidal Compositions on Several Key Broadleaf Weeds in Cereal Crops

| Application Rate (g/ha) | | | | | | | | | |
|---|---|---|---|---|---|---|---|---|---|
| Compound | Pyrasulfotole + | MATCH | | KCHSC | | VERPE | | VIOTR | |
| A K-salt | Bromoxynil | Ob | Ex | Ob | Ex | Ob | Ex | Ob | Ex |
| 8.75 | 0 | 50 | — | 67 | — | 73 | — | | |
| 17.5 | 0 | 62 | — | 77 | — | 78 | — | | |
| 35 | 0 | 57 | — | 90 | — | 83 | — | | |
| 0 | 25.6 | 23 | — | 58 | — | 30 | — | | |
| 8.75 | 25.6 | 73 | 62 | 90 | 86 | 88 | 81 | | |
| 17.5 | 25.6 | 70 | 71 | 93 | 90 | 90 | 85 | | |
| 35 | 25.6 | 78 | 67 | 92 | 96 | 92 | 88 | | |
| 0 | 51.3 | 37 | — | 78 | — | 30 | — | 83 | — |
| 8.75 | 51.3 | 80 | 68 | 97 | 93 | 87 | 81 | 93 | 87 |
| 17.5 | 51.3 | 84 | 76 | 100 | 95 | 95 | 85 | 95 | 91 |
| 35 | 51.3 | 87 | 73 | 98 | 98 | 98 | 88 | 88 | 90 |

ALOMY = *Alopecurus myosuroides*
APESV = *Apera spica-venti*
AVEFA = *Avena fatua*
MATCH = *Matricaria chamomila*
STEME = *Stellaria media*
VIOTR = *Viola tricolor*
CIRAR = *Cirsium arvense*
PHAMI = *Phalaris minor*
KCHSC = *Kochia scoparia*
POAAN = *Poa annua*
LOLRI = *Lolium rigidum*
BRSNI = *Brassica nigra*
POLCO = *Polygonum convolvulus*
LOLMG = *Lolium multiflorum*
SETVI = *Setaria viridis*
CHEAL = *Chenopodium album*
SINAR = *Sinapis arvensis*
VERPE = *Veronica persica*
BRSNN = *Brassica napus*
POLPE = *Polygonum persicaria*
VERHE = *Veronica hederifolia*
BROTE = *Bromus tectorum*
LOLMU = *Lolium multiflorum*
PESGL = *Pennisetum americanum*
GERDI = *Geranium dissectum*
SASKR = *Salsola iberica*

Evaluation of Postemergence Herbicidal Mixtures for Weed Control in Direct Seeded Rice Seeds or nutlets of the desired test plant species were planted in a soil matrix prepared by mixing a loam soil (43 percent silt, 19 percent clay, and 38 percent sand, with a pH of about 8.1 and an organic matter content of about 1.5 percent) and river sand in an 80 to 20 ratio. The soil matrix was contained in plastic pots with a surface area of 139.7 $cm^2$. When required to ensure good germination and healthy plants, a fungicide treatment and/or other chemical or physical treatment was applied. The plants were grown for 10-17 days in a greenhouse with an approximate 14 hr photoperiod which was maintained at about 29° C. during the day and 26° C. during the night. Nutrients and water were added on a regular basis and supplemental lighting was provided with overhead metal halide 1000-Watt lamps as necessary. The plants were employed for testing when they reached the second or third true leaf stage.

Treatments consisted of esters (methyl, n-butyl or allyl) or salts (TEA [triethylammonium]) of 4-amino-3-chloro-6-(4-chloro-2-fluoro-3-methoxy -phenyl)pyridine-2-carboxylic acid (Compound A), 4-amino-3-chloro-6-(2,4-dichloro-3-methoxyphenyl)pyridine-2-carboxylic acid (Compound C), or 4-amino-3-chloro-6-(4-chloro-2-fluoro-3-ethoxyphenyl) pyridine-2-carboxylic acid (Compound D), and various herbicidal components alone and in combination. Weighed amounts were placed in 25 mL glass vials and dissolved in a volume of 97:3 v/v acetone/DMSO to obtain 12× stock solutions. If the test compound did not dissolve readily, the mixture was warmed and/or sonicated. The concentrated stock solutions were added to the spray solutions so that the final acetone and DMSO concentrations were 16.2% and 0.5%, respectively. Spray solutions were diluted to the appropriate final concentrations with the addition of 10 mL of an aqueous mixture of 1.5% (v/v) Agri-dex crop oil concentrate. The final spray solutions contained 1.25% (v/v) Agri-dex crop oil concentrate. Compound requirements are based upon a 12 mL application volume at a rate of 187 L/ha. Formulated compounds were applied to the plant material with an overhead Mandel track sprayer equipped with a 8002E nozzles calibrated to deliver 187 L/ha over an application area of 0.503 $m^2$ at a spray height of 18 inches (43 cm) above average plant canopy height. Control plants were sprayed in the same manner with the solvent blank.

Forms of compounds A, C, and D were applied on an acid equivalent basis. Other herbicidal components were applied on an active ingredient basis and included acetolactate synthase (ALS)-inhibiting herbicides penoxsulam (triazolopyrimidine chemical class) applied as Grasp SC, bispyribac-sodium (pyrimidinylbenzoate chemical class) applied as Regiment 80 DF, halosulfuron-methyl (sulfonylurea chemical class) applied as Permit, bensulfuron-methyl (sulfonylurea chemical class) applied as Londax, imazethapyr (imidazolinone chemical class) applied as Newpath, and imazamox (imidazolinone chemical class) applied as Beyond; EPSP synthase inhibiting herbicide glyphosate applied as Glyphomax; photosystem II (PSII)-inhibiting herbicide propanil applied as Stam 80 EDF; protoporphyrinogen IX oxidase (Protox)-inhibiting herbicide carfentrazone-ethyl applied as Aim EC; acetyl CoA carboxylase (ACCase) inhibiting herbicides cyhalofop-butyl applied as Clincher SF and fenoxaprop-p-ethyl applied as Ricestar HT; auxinic herbicides triclopyr applied as Grandstand, MCPA EHE, and quinclorac applied as Facet 75 DF; auxin transport inhibiting herbicide diflufenzopyr; phytoene desaturase inhibiting herbicide norflurazon, p-hydroxyphenylpyruvate dioxygenase (HPPD) inhibiting herbicide sulcotrione applied as Mikado; other carotenoid biosynthesis inhibiting herbicides clomazone applied as Command 3 ME and pyriclor.

The treated plants and control plants were placed in a greenhouse as described above and watered by sub-irrigation to prevent wash-off of the test compounds. After 3 weeks, the condition of the test plants as compared with that of the untreated plants was determined visually and scored on a scale of 0 to 100 percent where 0 corresponds to no injury and 100 corresponds to complete kill.

Colby's equation was used to determine the herbicidal effects expected from the mixtures (Colby, S. R. 1967. Calculation of the synergistic and antagonistic response of herbicide combinations. Weeds 15:20-22.).

The following equation was used to calculate the expected activity of mixtures containing two active ingredients, A and B:

$$Expected=A+B-(A\times B/100)$$

A=observed efficacy of active ingredient A at the same concentration as used in the mixture.

B=observed efficacy of active ingredient B at the same concentration as used in the mixture.

Some of the herbicide combinations tested, application rates employed, plant species tested, and results are given in Tables 65-98.

TABLE 65

Synergistic Activity of Herbicidal Compositions on a Key Broadleaf Weed in Direct Seeded Rice
% Injury

| Application Rate (g/ha) | | | | Application Rate (g/ha) | | | |
|---|---|---|---|---|---|---|---|
| Compound | | IPOHE | | Compound | | IPOHE | |
| A Methyl | Penoxsulam | Ob | Ex | C Methyl | Penoxsulam | Ob | Ex |
| 4.38 | 0 | 10 | — | 4.38 | 0 | 40 | — |
| 8.75 | 0 | 15 | — | 8.75 | 0 | 70 | — |
| 0 | 4.38 | 70 | — | 0 | 4.38 | 70 | — |
| 0 | 8.75 | 60 | — | 0 | 8.75 | 60 | — |
| 4.38 | 4.38 | 100 | 73 | 4.38 | 4.38 | 75 | 82 |
| 8.75 | 4.38 | 90 | 75 | 8.75 | 4.38 | 95 | 91 |
| 4.38 | 8.75 | 75 | 64 | 4.38 | 8.75 | 90 | 76 |
| 8.75 | 8.75 | 90 | 66 | 8.75 | 8.75 | 85 | 88 |

TABLE 66

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | LEFCH | | Compound | | LEFCH | |
| A Methyl | Penoxsulam | Ob | Ex | A n-Butyl | Penoxsulam | Ob | Ex |
| 8.75 | 0 | 40 | — | 8.75 | 0 | 10 | — |
| 0 | 17.5 | 0 | — | 17.5 | 0 | 30 | — |
| 0 | 35 | 0 | — | 0 | 35 | 0 | — |
| 8.75 | 17.5 | 80 | 40 | 8.75 | 35 | 20 | 10 |
| 8.75 | 35 | 75 | 40 | 17.5 | 35 | 60 | 30 |

TABLE 67

Synergistic Activity of Herbicidal Compositions on a Key Sedge Weed in Direct Seeded Rice
% Injury

| Application Rate (g/ha) | | | | Application Rate (g/ha) | | | |
|---|---|---|---|---|---|---|---|
| Compound | | CYPES | | Compound | | CYPES | |
| A Methyl | Penoxsulam | Ob | Ex | A n-Butyl | Penoxsulam | Ob | Ex |
| 4.38 | 0 | 70 | — | 8.75 | 0 | 50 | — |
| 8.75 | 0 | 30 | — | 17.5 | 0 | 85 | — |
| 0 | 17.5 | 10 | — | 0 | 17.5 | 10 | — |
| 4.38 | 17.5 | 95 | 73 | 8.75 | 17.5 | 90 | 55 |
| 8.75 | 17.5 | 95 | 37 | 17.5 | 17.5 | 99 | 87 |

TABLE 67-continued

| Synergistic Activity of Herbicidal Compositions on a Key Sedge Weed in Direct Seeded Rice | | | |
|---|---|---|---|
| % Injury | | | |
| Application Rate (g/ha) | | | |
| Compound C Methyl | Penoxsulam | CYPES Ob | CYPES Ex |
| 8.75 | 0 | 30 | — |
| 17.5 | 0 | 65 | — |
| 0 | 17.5 | 10 | — |
| 8.75 | 17.5 | 95 | 37 |
| 17.5 | 17.5 | 90 | 69 |

TABLE 68

Synergistic Activity of Herbicidal Compositions on a Key Broadleaf Weed in Direct Seeded Rice % Injury

| Application Rate (g/ha) | | | | Application Rate (g/ha) | | | |
|---|---|---|---|---|---|---|---|
| Compound A Methyl | Bispyribac-sodium | IPOHE Ob | IPOHE Ex | Compound A n-Butyl | Bispyribac-sodium | IPOHE Ob | IPOHE Ex |
| 4.38 | 0 | 0 | — | 8.75 | 0 | 35 | — |
| 8.75 | 0 | 10 | — | 17.5 | 0 | 30 | — |
| 0 | 7 | 10 | — | 0 | 7 | 10 | — |
| 0 | 14 | 50 | — | 0 | 14 | 15 | — |
| 0 | 28 | 60 | — | 17.5 | 7 | 55 | 37 |
| 4.38 | 7 | 20 | 10 | 8.75 | 14 | 100 | 45 |
| 8.75 | 7 | 50 | 10 | 17.5 | 14 | 95 | 41 |
| 4.38 | 14 | 75 | 50 | | | | |
| 8.75 | 14 | 60 | 55 | | | | |
| 4.38 | 28 | 90 | 60 | | | | |
| 8.75 | 28 | 95 | 64 | | | | |

% Injury

| Application Rate (g/ha) | | | |
|---|---|---|---|
| Compound C Methyl | Bispyribac-sodium | IPOHE Ob | IPOHE Ex |
| 8.75 | 0 | 30 | — |
| 17.5 | 0 | 50 | — |
| 0 | 7 | 10 | — |
| 0 | 14 | 15 | — |
| 8.75 | 7 | 45 | 37 |
| 17.5 | 7 | 80 | 55 |
| 8.75 | 14 | 50 | 41 |
| 17.5 | 14 | 90 | 58 |

TABLE 69

Synergistic Activity of Herbicidal Compositions on Key Sedge Weeds in Direct Seeded Rice
% Injury

| Application Rate (g/ha) | | | | | | Application Rate (g/ha) | | | |
|---|---|---|---|---|---|---|---|---|---|
| Compound A Methyl | Bispyribac-sodium | CYPES Ob | CYPES Ex | CYPIR Ob | CYPIR Ex | Compound C Methyl | Bispyribac-sodium | CYPIR Ob | CYPIR Ex |
| 4.38 | 0 | 85 | — | 70 | — | 8.75 | 0 | 25 | — |
| 8.75 | 0 | 90 | — | 70 | — | 17.5 | 0 | 40 | — |

TABLE 69-continued

Synergistic Activity of Herbicidal Compositions on Key Sedge Weeds in Direct Seeded Rice
% Injury

| Application Rate (g/ha) | | CYPES | | CYPIR | | Application Rate (g/ha) | | CYPIR | |
|---|---|---|---|---|---|---|---|---|---|
| Compound A Methyl | Bispyribac-sodium | Ob | Ex | Ob | Ex | Compound C Methyl | Bispyribac-sodium | Ob | Ex |
| 0 | 14 | 0 | — | 90 | — | 0 | 7 | 40 | — |
| 0 | 28 | 50 | — | 95 | — | 0 | 14 | 90 | — |
| 4.38 | 14 | 90 | 85 | 95 | 97 | 8.75 | 7 | 99 | 55 |
| 8.75 | 14 | 100 | 90 | 99 | 97 | 17.5 | 7 | 95 | 64 |
| 4.38 | 28 | 95 | 93 | 100 | 99 | 8.75 | 14 | 100 | 93 |
| 8.75 | 28 | 100 | 95 | 95 | 99 | 17.5 | 14 | 100 | 94 |

TABLE 70

Synergistic Activity of Herbicidal Compositions on a Key Grass Weed in Direct Seeded Rice
% Injury

| Application Rate (g/ha) | | LEFCH | | Application Rate (g/ha) | | LEFCH | |
|---|---|---|---|---|---|---|---|
| Compound A Methyl | Halosulfuron-methyl | Ob | Ex | Compound A n-Butyl | Halosulfuron-methyl | Ob | Ex |
| 8.75 | 0 | 40 | — | 17.5 | 0 | 30 | — |
| 0 | 26 | 0 | — | 35 | 0 | 60 | — |
| 0 | 52 | 0 | — | 0 | 26 | 0 | — |
| 8.75 | 26 | 50 | 40 | 0 | 52 | 0 | — |
| 8.75 | 52 | 60 | 40 | 17.5 | 26 | 45 | 30 |
| | | | | 35 | 26 | 95 | 60 |
| | | | | 17.5 | 52 | 40 | 30 |
| | | | | 35 | 52 | 85 | 60 |

TABLE 71

Synergistic Activity of Herbicidal Compositions on a Key Grass Weed in Direct Seeded Rice
% Injury

| Application Rate (g/ha) | | LEFCH | | Application Rate (g/ha) | | LEFCH | |
|---|---|---|---|---|---|---|---|
| Compound A Methyl | Bensulfuron-methyl | Ob | Ex | Compound C Methyl | Bensulfuron-methyl | Ob | Ex |
| 4.38 | 0 | 30 | — | 4.38 | 0 | 0 | — |
| 0 | 4.38 | 20 | — | 0 | 4.38 | 20 | — |
| 0 | 8.75 | 0 | — | 0 | 8.75 | 0 | — |
| 4.38 | 4.38 | 55 | 44 | 4.38 | 4.38 | 45 | 20 |
| 4.38 | 8.75 | 99 | 30 | 4.38 | 8.75 | 55 | 0 |

TABLE 72

Synergistic Activity of Herbicidal Compositions on a Key Grass Weed in Direct Seeded Rice
% Injury

| Application Rate (g/ha) | | ISCRU | | Application Rate (g/ha) | | ISCRU | |
|---|---|---|---|---|---|---|---|
| Compound A Methyl | Imazethapyr | Ob | Ex | Compound A n-Butyl | Imazethapyr | Ob | Ex |
| 8.75 | 0 | 50 | — | 35 | 0 | 20 | — |
| 17.5 | 0 | 55 | — | 70 | 0 | 50 | — |
| 0 | 35 | 20 | — | 0 | 35 | 20 | — |

TABLE 72-continued

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | ISCRU | | Compound | | ISCRU | |
| A Methyl | Imazethapyr | Ob | Ex | A n-Butyl | Imazethapyr | Ob | Ex |
| 8.75 | 35 | 90 | 60 | 35 | 35 | 70 | 36 |
| 17.5 | 35 | 90 | 64 | 70 | 35 | 95 | 60 |

TABLE 73

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | ISCRU | | Compound | | ISCRU | |
| A Methyl | Imazamox | Ob | Ex | A n-Butyl | Imazamox | Ob | Ex |
| 8.75 | 0 | 50 | — | 35 | 0 | 20 | — |
| 17.5 | 0 | 55 | — | 70 | 0 | 50 | — |
| 0 | 22.4 | 50 | — | 0 | 22.4 | 50 | — |

TABLE 73-continued

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | ISCRU | | Compound | | ISCRU | |
| A Methyl | Imazamox | Ob | Ex | A n-Butyl | Imazamox | Ob | Ex |
| 8.75 | 22.4 | 80 | 75 | 35 | 22.4 | 85 | 60 |
| 17.5 | 22.4 | 95 | 78 | 70 | 22.4 | 100 | 75 |

TABLE 74

Synergistic Activity of Herbicidal Compositions on Key Broadleaf Weeds in Direct Seeded Rice
% Injury

| Application Rate (g/ha) | | | | | | Application Rate (g/ha) | | | | | |
|---|---|---|---|---|---|---|---|---|---|---|---|
| Compound | | IPOHE | | POLPE | | Compound | | IPOHE | | POLPE | |
| A Methyl | Propanil | Ob | Ex | Ob | Ex | C Methyl | Propanil | Ob | Ex | Ob | Ex |
| 8.75 | 0 | 85 | — | 50 | — | 35 | 0 | 65 | — | 85 | — |
| 17.5 | 0 | 85 | — | 90 | — | 70 | 0 | 85 | — | 100 | — |
| 0 | 560 | 10 | — | 10 | — | 0 | 560 | 10 | — | 10 | — |
| 0 | 1120 | 10 | — | 40 | — | 0 | 1120 | 10 | — | 40 | — |
| 8.75 | 560 | 95 | 87 | 100 | 55 | 35 | 560 | 70 | 69 | 100 | 87 |
| 17.5 | 560 | 100 | 87 | 80 | 91 | 70 | 560 | 90 | 87 | 100 | 100 |
| 8.75 | 1120 | 100 | 87 | 100 | 70 | 35 | 1120 | 95 | 69 | 100 | 91 |
| 17.5 | 1120 | 95 | 87 | 70 | 94 | 70 | 1120 | 100 | 87 | 100 | 100 |

TABLE 75

Synergistic Speed of Activity of Herbicidal Compositions on Key Sedge Weeds in Direct Seeded Rice

| % Injury at 11 DAA | | | | | | % Injury at 21 DAA | | | | | |
|---|---|---|---|---|---|---|---|---|---|---|---|
| Application Rate (g/ha) | | | | | | Application Rate (g/ha) | | | | | |
| Compound | | CYPIR | | SCPMA | | Compound | | CYPIR | | SCPMA | |
| A n-Butyl | Propanil | Ob | Ex | Ob | Ex | A n-Butyl | Propanil | Ob | Ex | Ob | Ex |
| 35 | 0 | 60 | — | 30 | — | 35 | 0 | 60 | — | 50 | — |
| 70 | 0 | 90 | — | 100 | — | 70 | 0 | 100 | — | 100 | — |
| 0 | 560 | 10 | — | 30 | — | 0 | 560 | 0 | — | 0 | — |
| 0 | 1120 | 10 | — | 30 | — | 0 | 1120 | 0 | — | 0 | — |
| 35 | 560 | 100 | 64 | 50 | 51 | 35 | 560 | 100 | 60 | 50 | 50 |
| 70 | 560 | 95 | 91 | 100 | 100 | 70 | 560 | 99 | 100 | 100 | 100 |
| 35 | 1120 | 90 | 64 | 90 | 51 | 35 | 1120 | 99 | 60 | 100 | 50 |
| 70 | 1120 | 100 | 91 | 95 | 100 | 70 | 1120 | 100 | 100 | 100 | 100 |

TABLE 76

Synergistic Activity of Herbicidal Compositions on a Key Broadleaf Weed in Direct Seeded Rice % Injury

| Application Rate (g/ha) | | POLPE | |
|---|---|---|---|
| Compound A n-Butyl | Carfentrazone-ethyl | Ob | Ex |
| 4.38 | 0 | 40 | — |
| 8.75 | 0 | 60 | — |
| 0 | 14 | 0 | — |
| 4.38 | 14 | 50 | 40 |
| 8.75 | 14 | 100 | 60 |

TABLE 77

Synergistic Activity of Herbicidal Compositions on Key Sedge Weeds in Direct Seeded Rice % Injury

| Application Rate (g/ha) | | CYPES | | Application Rate (g/ha) | | CYPES | |
|---|---|---|---|---|---|---|---|
| Compound A Methyl | Carfentrazone-ethyl | Ob | Ex | Compound A n-Butyl | Carfentrazone-ethyl | Ob | Ex |
| 4.38 | 0 | 85 | — | 8.75 | 0 | 50 | — |
| 8.75 | 0 | 90 | — | 17.5 | 0 | 90 | — |
| 0 | 56 | 10 | — | 0 | 56 | 10 | — |
| 0 | 112 | 0 | — | 0 | 112 | 0 | — |
| 4.38 | 56 | 100 | 87 | 8.75 | 56 | 85 | 55 |
| 8.75 | 56 | 100 | 91 | 17.5 | 56 | 90 | 91 |
| 4.38 | 112 | 100 | 85 | 8.75 | 112 | 100 | 50 |
| 8.75 | 112 | 100 | 90 | 17.5 | 112 | 100 | 90 |

% Injury

| Application Rate (g/ha) | | CYPES | | Application Rate (g/ha) | | CYPIR | |
|---|---|---|---|---|---|---|---|
| Compound C Methyl | Carfentrazone-ethyl | Ob | Ex | Compound C Methyl | Carfentrazone-ethyl | Ob | Ex |
| 8.75 | 0 | 65 | — | 8.75 | 0 | 25 | — |
| 17.5 | 0 | 100 | — | 17.5 | 0 | 40 | — |
| 0 | 56 | 10 | — | 0 | 14 | 0 | — |
| 0 | 112 | 0 | — | 0 | 28 | 0 | — |
| 8.75 | 56 | 100 | 68 | 8.75 | 14 | 50 | 25 |
| 17.5 | 56 | 85 | 100 | 17.5 | 28 | 100 | 40 |
| 8.75 | 112 | 100 | 65 | | | | |
| 17.5 | 112 | 99 | 100 | | | | |

TABLE 78

Synergistic Speed of Activity of Herbicidal Compositions on a Key Sedge Weed in Direct Seeded Rice % Injury

| Application Rate (g/ha) | | 11 DAA CYPES | | 21 DAA CYPES | |
|---|---|---|---|---|---|
| Compound A Methyl | Carfentrazone-ethyl | Ob | Ex | Ob | Ex |
| 8.75 | 0 | 60 | — | 100 | — |
| 17.5 | 0 | 70 | — | 99 | — |
| 0 | 14 | 10 | — | 0 | — |
| 0 | 28 | 10 | — | 0 | — |
| 8.75 | 14 | 100 | 64 | 95 | 100 |

TABLE 78-continued

Synergistic Speed of Activity of Herbicidal Compositions on a Key Sedge Weed in Direct Seeded Rice

| | | | | | |
|---|---|---|---|---|---|
| 17.5 | 14 | 100 | 73 | 99 | 99 |
| 8.75 | 28 | 100 | 64 | 100 | 100 |
| 17.5 | 28 | 70 | 73 | 80 | 99 |

% Injury

| Application Rate (g/ha) | | 11 DAA CYPES | | 21 DAA CYPES | |
|---|---|---|---|---|---|
| Compound A n-Butyl | Carfentrazone-ethyl | Ob | Ex | Ob | Ex |
| 35 | 0 | 50 | — | 90 | — |
| 70 | 0 | 75 | — | 100 | — |
| 0 | 14 | 10 | — | 0 | — |

TABLE 78-continued

Synergistic Speed of Activity of Herbicidal Compositions on a Key Sedge Weed in Direct Seeded Rice

| | | | | | |
|---|---|---|---|---|---|
| 0 | 28 | 10 | — | 0 | — |
| 35 | 14 | 70 | 55 | 85 | 90 |
| 70 | 14 | 80 | 78 | 99 | 100 |
| 35 | 28 | 100 | 55 | 100 | 90 |
| 70 | 28 | 100 | 78 | 100 | 100 |

TABLE 79

Synergistic Activity of Herbicidal Compositions on Key Broadleaf Weeds in Direct Seeded Rice % Injury

| Application Rate (g/ha) | | | | Application Rate (g/ha) | | | |
|---|---|---|---|---|---|---|---|
| Compound A Methyl | Cyhalofop-butyl | IPOHE Ob | IPOHE Ex | Compound C Methyl | Cyhalofop-butyl | IPOHE Ob | IPOHE Ex |
| 8.75 | 0 | 40 | — | 8.75 | 0 | 10 | — |
| 17.5 | 0 | 75 | — | 17.5 | 0 | 40 | — |
| 0 | 280 | 0 | — | 35 | 0 | 20 | — |
| 8.75 | 280 | 90 | 40 | 0 | 140 | 0 | — |
| 17.5 | 280 | 90 | 75 | 0 | 280 | 0 | — |
| | | | | 8.75 | 140 | 85 | 10 |
| | | | | 17.5 | 140 | 85 | 40 |
| | | | | 35 | 140 | 90 | 20 |
| | | | | 8.75 | 280 | 40 | 10 |
| | | | | 17.5 | 280 | 90 | 40 |
| | | | | 35 | 280 | 90 | 20 |

% Injury

| Application Rate (g/ha) | | | | Application Rate (g/ha) | | | |
|---|---|---|---|---|---|---|---|
| Compound A Methyl | Cyhalofop-butyl | POLPY Ob | POLPY Ex | Compound A n-Butyl | Cyhalofop-butyl | POLPY Ob | POLPY Ex |
| 4.38 | 0 | 50 | — | 8.75 | 0 | 40 | — |
| 8.75 | 0 | 60 | — | 17.5 | 0 | 90 | — |
| 0 | 100 | 0 | — | 0 | 100 | 0 | — |
| 4.38 | 100 | 0 | — | 8.75 | 100 | 0 | — |
| 8.75 | 100 | 40 | 50 | 17.5 | 100 | 55 | 40 |
| 0 | 200 | 50 | 60 | 0 | 200 | 95 | 90 |
| 4.38 | 200 | 65 | 50 | 8.75 | 200 | 80 | 40 |
| 8.75 | 200 | 75 | 60 | 17.5 | 200 | 95 | 90 |

% Injury

| Application Rate (g/ha) | | | |
|---|---|---|---|
| Compound C Methyl | Cyhalofop-butyl | POLPY Ob | POLPY Ex |
| 8.75 | 0 | 10 | — |
| 17.5 | 0 | 15 | — |
| 0 | 100 | 0 | — |
| 8.75 | 100 | 0 | — |
| 17.5 | 100 | 20 | 10 |
| 0 | 200 | 35 | 15 |
| 8.75 | 200 | 10 | 10 |
| 17.5 | 200 | 30 | 15 |

TABLE 80

Synergistic Activity of Herbicidal Compositions on Key Sedge Weeds in Direct Seeded Rice % Injury

| Application Rate (g/ha) | | CYPES | | Application Rate (g/ha) | | CYPIR | |
|---|---|---|---|---|---|---|---|
| Compound C Methyl | Cyhalofop-butyl | Ob | Ex | Compound A Methyl | Cyhalofop-butyl | Ob | Ex |
| 8.75 | 0 | 30 | — | 8.75 | 0 | 30 | — |
| 17.5 | 0 | 65 | — | 35 | 0 | 50 | — |
| 0 | 100 | 0 | — | 0 | 140 | 0 | — |
| 0 | 200 | 0 | — | 0 | 280 | 0 | — |
| 8.75 | 100 | 85 | 30 | 8.75 | 140 | 40 | 30 |
| 17.5 | 100 | 85 | 65 | 35 | 140 | 85 | 50 |
| 8.75 | 200 | 95 | 30 | 8.75 | 280 | 35 | 30 |
| 17.5 | 200 | 95 | 65 | 35 | 280 | 75 | 50 |

% Injury

| Application Rate (g/ha) | | CYPIR | | Application Rate (g/ha) | | CYPIR | |
|---|---|---|---|---|---|---|---|
| Compound C Methyl | Cyhalofop-butyl | Ob | Ex | Compound D Methyl | Cyhalofop-butyl | Ob | Ex |
| 17.5 | 0 | 0 | — | 8.75 | 0 | 50 | — |
| 35 | 0 | 40 | — | 35 | 0 | 80 | — |
| 0 | 140 | 0 | — | 0 | 140 | 0 | — |
| 0 | 280 | 0 | — | 0 | 280 | 0 | — |
| 17.5 | 140 | 25 | 0 | 8.75 | 140 | 60 | 50 |
| 35 | 140 | 80 | 40 | 35 | 140 | 75 | 80 |
| 17.5 | 280 | 50 | 0 | 8.75 | 280 | 70 | 50 |
| 35 | 280 | 70 | 40 | 35 | 280 | 95 | 80 |

TABLE 81

Synergistic Activity of Herbicidal Compositions on a Key Broadleaf Weed in Direct Seeded Rice % Injury

| Application Rate (g/ha) | | POLPY | |
|---|---|---|---|
| Compound A Allyl | Fenoxaprop-p-ethyl | Ob | Ex |
| 17.5 | 0 | 70 | — |
| 0 | 35 | 0 | — |
| 17.5 | 35 | 85 | 70 |

TABLE 82

Synergistic Activity of Herbicidal Compositions on Key Sedge Weeds in Direct Seeded Rice % Injury

| Application Rate (g/ha) | | FIMMI | | SCPMA | |
|---|---|---|---|---|---|
| Compound A Allyl | Fenoxaprop-p-ethyl | Ob | Ex | Ob | Ex |
| 17.5 | 0 | 40 | — | 0 | — |
| 0 | 35 | 0 | — | 0 | — |
| 17.5 | 35 | 95 | 40 | 40 | 0 |

TABLE 83

Synergistic Activity of Herbicidal Compositions on a Key Sedge Weed in Direct Seeded Rice % Injury

| Application Rate (g/ha) | | CYPES | |
|---|---|---|---|
| Compound C Methyl | Triclopyr-TEA | Ob | Ex |
| 8.75 | 0 | 65 | — |
| 0 | 140 | 0 | — |
| 0 | 280 | 0 | — |
| 8.75 | 140 | 100 | 65 |
| 8.75 | 280 | 90 | 65 |

TABLE 84

Synergistic Activity of Herbicidal Compositions on Key Grass Weeds in Direct Seeded Rice % Injury

| Application Rate (g/ha) | | BRAPP | | ISCRU | |
|---|---|---|---|---|---|
| Compound A Allyl | MCPA EHE | Ob | Ex | Ob | Ex |
| 8.75 | 0 | 60 | — | 10 | — |
| 17.5 | 0 | 99 | — | 40 | — |
| 0 | 70 | 0 | — | 0 | — |
| 0 | 140 | 0 | — | 0 | — |
| 8.75 | 70 | 80 | 60 | 0 | 10 |
| 17.5 | 70 | 70 | 99 | 20 | 40 |
| 8.75 | 140 | 100 | 60 | 50 | 10 |
| 17.5 | 140 | 85 | 99 | 50 | 40 |

TABLE 85

| Synergistic Activity of Herbicidal Compositions on a Key Sedge Weed in Direct Seeded Rice % Injury | | | |
|---|---|---|---|
| Application Rate (g/ha) | | | |
| Compound | MCPA | FIMMI | |
| A Allyl | EHE | Ob | Ex |
| 8.75 | 0 | 0 | — |
| 17.5 | 0 | 20 | — |
| 0 | 70 | 0 | — |
| 0 | 140 | 0 | — |
| 8.75 | 70 | 40 | 0 |
| 17.5 | 70 | 30 | 20 |
| 8.75 | 140 | 80 | 0 |
| 17.5 | 140 | 95 | 20 |

TABLE 86

| Synergistic Activity of Herbicidal Compositions on Key Sedge Weeds in Direct Seeded Rice % Injury | | | | | | | |
|---|---|---|---|---|---|---|---|
| Application Rate (g/ha) | | | | Application Rate (g/ha) | | | |
| Compound | | CYPIR | | Compound | | FIMMI | |
| A Methyl | Quinclorac | Ob | Ex | A Allyl | Quinclorac | Ob | Ex |
| 4.38 | 0 | 30 | — | 8.75 | 0 | 0 | — |
| 8.75 | 0 | 75 | — | 17.5 | 0 | 40 | — |
| 0 | 140 | 0 | — | 0 | 140 | 0 | — |
| 4.38 | 140 | 70 | 30 | 8.75 | 140 | 60 | 0 |
| 8.75 | 140 | 85 | 75 | 17.5 | 140 | 100 | 40 |

TABLE 87

| Synergistic Activity of Herbicidal Compositions on a Key Broadleaf Weed in Direct Seeded Rice % Injury | | | |
|---|---|---|---|
| Application Rate (g/ha) | | | |
| Compound | | IPOHE | |
| A Methyl | Diflufenzopyr | Ob | Ex |
| 4.38 | 0 | 20 | — |
| 8.75 | 0 | 40 | — |
| 17.5 | 0 | 75 | — |
| 0 | 4.38 | 10 | — |
| 0 | 8.75 | 40 | — |
| 0 | 17.5 | 60 | — |
| 0 | 35 | 65 | — |
| 4.38 | 4.38 | 30 | 28 |
| 8.75 | 4.38 | 65 | 46 |
| 17.5 | 4.38 | 90 | 78 |
| 4.38 | 8.75 | 65 | 52 |
| 8.75 | 8.75 | 65 | 64 |
| 17.5 | 8.75 | 80 | 85 |
| 4.38 | 17.5 | 75 | 68 |
| 8.75 | 17.5 | 90 | 76 |
| 17.5 | 17.5 | 95 | 90 |
| 4.38 | 35 | 70 | 72 |
| 8.75 | 35 | 85 | 79 |
| 17.5 | 35 | 95 | 91 |

TABLE 88

Synergistic Activity of Herbicidal Compositions on a Key Grass Weed in Direct Seeded Rice
% Injury

| Application Rate (g/ha) | | | |
|---|---|---|---|
| Compound | | LEFCH | |
| A Methyl | Diflufenzopyr | Ob | Ex |
| 4.38 | 0 | 30 | — |
| 8.75 | 0 | 80 | — |
| 17.5 | 0 | 75 | — |
| 35 | 0 | 90 | — |
| 0 | 8.75 | 0 | — |
| 4.38 | 8.75 | 45 | 30 |
| 8.75 | 8.75 | 90 | 80 |
| 17.5 | 8.75 | 95 | 75 |
| 35 | 8.75 | 90 | 90 |

TABLE 89

Synergistic Activity of Herbicidal Compositions on a Key Sedge Weed in Direct Seeded Rice
% Injury

| Application Rate (g/ha) | | | |
|---|---|---|---|
| Compound | | CYPIR | |
| A Methyl | Diflufenzopyr | Ob | Ex |
| 8.75 | 0 | 30 | — |
| 35 | 0 | 50 | — |
| 0 | 4.38 | 10 | — |
| 0 | 8.75 | 15 | — |
| 0 | 17.5 | 20 | — |
| 0 | 35 | 30 | — |
| 8.75 | 4.38 | 25 | 37 |
| 35 | 4.38 | 85 | 55 |
| 8.75 | 8.75 | 55 | 41 |
| 35 | 8.75 | 90 | 58 |
| 8.75 | 17.5 | 60 | 44 |
| 35 | 17.5 | 95 | 60 |
| 8.75 | 35 | 60 | 51 |
| 35 | 35 | 95 | 65 |

TABLE 90

Synergistic Activity of Herbicidal Compositions on a Key Grass Weed in Direct Seeded Rice
% Injury

| Application Rate (g/ha) | | | |
|---|---|---|---|
| Compound | | LEFCH | |
| A Methyl | Clomazone | Ob | Ex |
| 4.38 | 0 | 10 | — |
| 17.5 | 0 | 50 | — |
| 0 | 560 | 40 | — |
| 4.38 | 560 | 85 | 46 |
| 17.5 | 560 | 99 | 70 |

TABLE 91

Synergistic Activity of Herbicidal Compositions on a Key Sedge Weed in Direct Seeded Rice
% Injury

| Application Rate (g/ha) | | | |
|---|---|---|---|
| Compound | | CYPIR | |
| A Methyl | Clomazone | Ob | Ex |
| 4.38 | 0 | 80 | — |
| 0 | 560 | 0 | — |
| 0 | 1120 | 0 | — |
| 4.38 | 560 | 90 | 80 |
| 4.38 | 1120 | 100 | 80 |

TABLE 92

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | BRAPP | | Compound | | BRAPP | |
| A Methyl | Norflurazon | Ob | Ex | A Allyl | Norflurazon | Ob | Ex |
| 8.75 | 0 | 60 | — | 8.75 | 0 | 80 | — |
| 0 | 70 | 0 | — | 0 | 70 | 0 | — |
| 8.75 | 70 | 90 | 60 | 8.75 | 70 | 95 | 80 |

TABLE 93

Synergistic Activity of Herbicidal Compositions on Key Sedge Weeds in Direct Seeded Rice % Injury

| Application Rate (g/ha) | | | | | | | | | |
|---|---|---|---|---|---|---|---|---|---|
| Compound | | CYPES | | CYPIR | | FIMMI | | SCPMA | |
| A Methyl | Norflurazon | Ob | Ex | Ob | Ex | Ob | Ex | Ob | Ex |
| 4.38 | 0 | 40 | — | 25 | — | 20 | — | 0 | — |
| 8.75 | 0 | 60 | — | 50 | — | 40 | — | 10 | — |
| 0 | 560 | 0 | — | 0 | — | 0 | — | 60 | — |
| 4.38 | 560 | 90 | 40 | 20 | 25 | 65 | 20 | 80 | 60 |
| 8.75 | 560 | 99 | 60 | 90 | 50 | 90 | 40 | 90 | 64 |

% Injury

| Application Rate (g/ha) | | | | | | | | | |
|---|---|---|---|---|---|---|---|---|---|
| Compound | | CYPES | | CYPIR | | FIMMI | | SCPMA | |
| A Allyl | Norflurazon | Ob | Ex | Ob | Ex | Ob | Ex | Ob | Ex |
| 17.5 | 0 | 50 | — | 35 | — | 50 | — | 10 | — |
| 35 | 0 | 95 | — | 85 | — | 60 | — | 20 | — |
| 0 | 560 | 0 | — | 0 | — | 0 | — | 60 | — |
| 17.5 | 560 | 90 | 50 | 60 | 35 | 70 | 50 | 70 | 64 |
| 35 | 560 | 100 | 95 | 70 | 85 | 70 | 60 | 99 | 68 |

TABLE 94

Synergistic Activity of Herbicidal Compositions on a Key Grass Weed in Direct Seeded Rice
% Injury

| Application Rate (g/ha) | | | | Application Rate (g/ha) | | | |
|---|---|---|---|---|---|---|---|
| Compound | | BRAPP | | Compound | | BRAPP | |
| A Methyl | Sulcotrione | Ob | Ex | A Allyl | Sulcotrione | Ob | Ex |
| 4.38 | 0 | 60 | — | 4.38 | 0 | 80 | — |
| 8.75 | 0 | 60 | — | 8.75 | 0 | 100 | — |
| 0 | 70 | 15 | — | 0 | 70 | 70 | — |
| 4.38 | 70 | 60 | 66 | 4.38 | 70 | 99 | 83 |
| 8.75 | 70 | 85 | 66 | 8.75 | 70 | 100 | 100 |

TABLE 95

Synergistic Activity of Herbicidal Compositions on a Key Grass Weed in Direct Seeded Rice
% Injury

| Application Rate (g/ha) | | | |
|---|---|---|---|
| Compound | | DIGSA | |
| A Methyl | Pyriclor | Ob | Ex |
| 4.38 | 0 | 40 | — |
| 17.5 | 0 | 50 | — |
| 0 | 140 | 80 | — |
| 4.38 | 140 | 99 | 88 |
| 17.5 | 140 | 100 | 90 |

TABLE 96

Synergistic Activity of Herbicidal Compositions on a Key Broadleaf Weed in Direct Seeded Rice
% Injury

| Application Rate (g/ha) | | | | Application Rate (g/ha) | | | |
|---|---|---|---|---|---|---|---|
| Compound | | POLPY | | Compound | | POLPY | |
| A Methyl | Glyphosate | Ob | Ex | A Allyl | Glyphosate | Ob | Ex |
| 4.38 | 0 | 10 | — | 17.5 | 0 | 90 | — |
| 8.75 | 0 | 50 | — | 35 | 0 | 70 | — |
| 0 | 70 | 0 | — | 0 | 70 | 0 | — |
| 4.38 | 70 | 40 | 10 | 17.5 | 70 | 95 | 90 |
| 8.75 | 70 | 60 | 50 | 35 | 70 | 90 | 70 |

TABLE 97

Synergistic Activity of Herbicidal Compositions on Key Grass Weeds in Direct Seeded Rice
% Injury

| Application Rate (g/ha) | | | | | |
|---|---|---|---|---|---|
| Compound | | DIGSA | | LEFCH | |
| A Methyl | Glyphosate | Ob | Ex | Ob | Ex |
| 4.38 | 0 | 0 | — | 20 | — |
| 8.75 | 0 | 20 | — | 30 | — |
| 0 | 70 | 0 | — | 20 | — |
| 4.38 | 70 | 60 | 0 | 50 | 35 |
| 8.75 | 70 | 80 | 20 | 40 | 44 |

TABLE 98

Synergistic Activity of Herbicidal Compositions on Key Sedge Weeds in Direct Seeded Rice
% Injury

| Application Rate (g/ha) | | | | | |
|---|---|---|---|---|---|
| Compound | | CYPES | | CYPIR | |
| A Allyl | Glyphosate | Ob | Ex | Ob | Ex |
| 17.5 | 0 | 50 | — | 35 | — |
| 35 | 0 | 95 | — | 85 | — |
| 0 | 70 | 10 | — | 0 | — |
| 17.5 | 70 | 90 | 55 | 65 | 35 |
| 35 | 70 | 95 | 96 | 100 | 85 |

Evaluation of Herbicidal Mixtures for Weed Control in Transplanted Paddy Rice Weed seeds or nutlets of the desired test plant species were planted in puddled soil (mud) prepared by mixing a non-sterilized mineral soil (28 percent silt, 18 percent clay, and 54 percent sand, with a pH of about 7.3 to 7.8 and an organic matter content of about 1.0 percent) and water at a ratio of 100 kilograms (kg) of soil to 19 L of water. The prepared mud was dispensed in 250 mL aliquots into 480 mL non-perforated plastic pots with a surface area of 91.6 square centimeters leaving a headspace of 3 centimeters in each pot. Rice seeds were planted in Sun Gro MetroMix® 306 planting mixture, which typically has a pH of 6.0 to 6.8 and an organic matter content of about 30 percent, in plastic plug trays. Seedlings at the second or third leaf stage of growth were transplanted into 650 mL of mud contained in 960 mL non-perforated plastic pots with a surface area of 91.6 $cm^2$ 4 days prior to herbicide application. The paddy was created by filling the 3 centimeter headspace of the pots with water. When required to ensure good germination and healthy plants, a fungicide treatment and/or other chemical or physical treatment was applied. The plants were grown for 4-14 days in a greenhouse with an approximate 14 hr photoperiod which was maintained at about 29° C. during the day and 26° C. during the night. Nutrients were added as Osmocote (17:6:10, N:P:K+minor nutrients) at 2 g per cup. Water was added on a regular basis to maintain the paddy flood, and supplemental lighting was provided with overhead metal halide 1000-Watt lamps as necessary. The plants were employed for testing when they reached the second or third true leaf stage.

Treatments consisted of esters or salts of compound A, compound C, or compound D and various herbicidal components alone and in combination. For technical grade compounds, a weighed amount, determined by the highest rate to be tested, was placed in an individual 120 mL glass vial and was dissolved in 20 mL of acetone to obtain concentrated stock solutions. If the test compound did not dissolve readily, the mixture was warmed and/or sonicated. The concentrated stock solutions obtained were diluted with 20 mL of an aqueous mixture containing 2.5% Agri-dex crop oil concentrate (v/v). For formulated compounds, a measured amount, determined by the highest rate to be tested, was placed in an individual 120 mL glass vial and was dissolved in 20 mL of 2.5% (v/v) Agri-dex crop oil concentrate to obtain concentrated stock solutions. The concentrated stock solutions obtained were diluted with 20 mL of acetone. Applications were made by injecting an appropriate amount of the stock solution into the aqueous layer of the paddy. Control plants were treated in the same manner with the solvent blank. All treated plant material received the same concentration of acetone and crop oil concentrate.

Forms of compounds A, C, and D were applied on an acid equivalent basis. Other herbicidal components were applied on an active ingredient basis and included acetolactate synthase (ALS)-inhibiting herbicides penoxsulam (triazolopyrimidine chemical class) applied as Grasp SC, pyrazosulfuron-methyl (sulfonylurea chemical class) applied as Sirius G, and bensulfuron-methyl (sulfonylurea chemical class) applied as Londax; acetyl CoA carboxylase (ACCase) inhibiting herbicides cyhalofop-butyl applied as Clincher G and fenoxaprop-p-ethyl applied as Ricestar HT; auxinic herbicide quinclorac applied as Facet 75 DF; phytoene desaturase inhibiting herbicide norflurazon; and p-hydroxyphenylpyruvate dioxygenase (HPPD) inhibiting herbicide sulcotrione applied as Mikado.

The treated plants and control plants were placed in a greenhouse as described above and water was added as needed to maintain a paddy flood. After 3 weeks the condition of the test plants as compared with that of the untreated plants was determined visually and scored on a scale of 0 to 100 percent where 0 corresponds to no injury and 100 corresponds to complete kill.

Some of the herbicide combinations tested, application rates employed, plant species tested, and results are given in Tables 99-113.

TABLE 99

Synergistic Activity of Herbicidal Compositions on Key Grass Weeds in Transplanted Paddy Rice

| % Injury | | | | | | | | | |
|---|---|---|---|---|---|---|---|---|---|
| Application Rate (g/ha) | | | | | | Application Rate (g/ha) | | | |
| Compound A Methyl | Bensulfuron-methyl | ECHCG Ob | ECHCG Ex | ECHCO Ob | ECHCO Ex | Compound C Methyl | Bensulfuron-methyl | ECHCG Ob | ECHCG Ex |
| 8.75 | 0 | 0 | — | 0 | — | 17.5 | 0 | 0 | — |
| 17.5 | 0 | 0 | — | 25 | — | 35 | 0 | 10 | — |
| 35 | 0 | 25 | — | 20 | — | 0 | 35 | 20 | — |
| 0 | 35 | 20 | — | 20 | — | 0 | 70 | 45 | — |
| 0 | 70 | 45 | — | 30 | — | 17.5 | 35 | 40 | 20 |
| 8.75 | 35 | 40 | 20 | 35 | 20 | 35 | 35 | 45 | 28 |
| 17.5 | 35 | 55 | 20 | 35 | 40 | 17.5 | 70 | 60 | 45 |
| 35 | 35 | 60 | 40 | 50 | 36 | 35 | 70 | 55 | 51 |
| 8.75 | 70 | 60 | 45 | 40 | 30 | | | | |
| 17.5 | 70 | 65 | 45 | 55 | 48 | | | | |
| 35 | 70 | 80 | 59 | 60 | 44 | | | | |

| % Injury | | | | | | | | | |
|---|---|---|---|---|---|---|---|---|---|
| Application Rate (g/ha) | | | | | | Application Rate (g/ha) | | | |
| Compound C TEA | Bensulfuron-methyl | ECHCG Ob | ECHCG Ex | LEFCH Ob | LEFCH Ex | Compound A TEA | Bensulfuron-methyl | ECHCG Ob | ECHCG Ex |
| 35 | 0 | 0 | — | 50 | — | 35 | 0 | 20 | — |
| 70 | 0 | 25 | — | 95 | — | 70 | 0 | 50 | — |
| 0 | 35 | 65 | — | 15 | — | 0 | 35 | 65 | — |
| 0 | 70 | 70 | — | 30 | — | 0 | 70 | 70 | — |
| 35 | 35 | 90 | 65 | 85 | 58 | 35 | 35 | 95 | 72 |
| 70 | 35 | 95 | 74 | 100 | 96 | 70 | 35 | 99 | 83 |
| 35 | 70 | 80 | 70 | 90 | 65 | 35 | 70 | 100 | 76 |
| 70 | 70 | 95 | 78 | 100 | 97 | 70 | 70 | 95 | 85 |

TABLE 100

Synergistic Activity of Herbicidal Compositions on Key Sedge Weeds in Transplanted Paddy Rice % Injury

| Application Rate (g/ha) | | | | Application Rate (g/ha) | | | | | |
|---|---|---|---|---|---|---|---|---|---|
| Compound A Methyl | Bensulfuron-methyl | CYPES Ob | CYPES Ex | Compound C TEA | Bensulfuron-methyl | ELOKU Ob | ELOKU Ex | FIMMI Ob | FIMMI Ex |
| 4.38 | 0 | 0 | — | 35 | 0 | 0 | — | 0 | — |
| 8.75 | 0 | 15 | — | 70 | 0 | 50 | — | 0 | — |
| 0 | 4.38 | 40 | — | 0 | 35 | 20 | — | 10 | — |
| 0 | 8.75 | 50 | — | 0 | 70 | 70 | — | 50 | — |
| 4.38 | 4.38 | 85 | 40 | 35 | 35 | 50 | 20 | 0 | 10 |
| 8.75 | 4.38 | 75 | 49 | 70 | 35 | 60 | 60 | 40 | 10 |
| 4.38 | 8.75 | 85 | 50 | 35 | 70 | 80 | 70 | 40 | 50 |
| 8.75 | 8.75 | 85 | 58 | 70 | 70 | 80 | 85 | 100 | 50 |

TABLE 101

Synergistic Activity of Herbicidal Compositions on a Key Grass Weed in Transplanted Paddy Rice
% Injury

| Application Rate (g/ha) | | ECHCG | | Application Rate (g/ha) | | ECHCG | |
|---|---|---|---|---|---|---|---|
| Compound A Methyl | Pyrazosulfuron-ethyl | Ob | Ex | Compound C Methyl | Pyrazosulfuron-ethyl | Ob | Ex |
| 4.38 | 0 | 0 | — | 4.38 | 0 | 0 | — |
| 8.75 | 0 | 25 | — | 8.75 | 0 | 0 | — |
| 0 | 5.25 | 20 | — | 0 | 5.25 | 20 | — |
| 4.38 | 5.25 | 35 | 20 | 4.38 | 5.25 | 45 | 20 |
| 8.75 | 5.25 | 80 | 40 | 8.75 | 5.25 | 20 | 20 |

TABLE 102

Synergistic Activity of Herbicidal Compositions on Key Grass Weeds in Transplanted Paddy Rice % Injury

| Application Rate (g/ha) | | ECHCG | | Application Rate (g/ha) | | ECHCG | |
|---|---|---|---|---|---|---|---|
| Compound A Methyl | Penoxsulam | Ob | Ex | Compound C Methyl | Penoxsulam | Ob | Ex |
| 4.38 | 0 | 0 | — | 4.38 | 0 | 0 | — |
| 8.75 | 0 | 25 | — | 8.75 | 0 | 0 | — |
| 0 | 4.38 | 70 | — | 0 | 4.38 | 70 | — |
| 4.38 | 4.38 | 90 | 70 | 4.38 | 4.38 | 95 | 70 |
| 8.75 | 4.38 | 95 | 78 | 8.75 | 4.38 | 70 | 70 |

% Injury

| Application Rate (g/ha) | | LEFCH | | Application Rate (g/ha) | | LEFCH | |
|---|---|---|---|---|---|---|---|
| Compound A Methyl | Penoxsulam | Ob | Ex | Compound C Methyl | Penoxsulam | Ob | Ex |
| 8.75 | 0 | 0 | — | 17.5 | 0 | 0 | — |
| 17.5 | 0 | 0 | — | 35 | 0 | 0 | — |
| 35 | 0 | 0 | — | 70 | 0 | 0 | — |
| 0 | 17.5 | 15 | — | 0 | 17.5 | 15 | — |
| 0 | 35 | 20 | — | 0 | 35 | 20 | — |
| 8.75 | 17.5 | 30 | 15 | 17.5 | 17.5 | 20 | 15 |
| 17.5 | 17.5 | 20 | 15 | 35 | 17.5 | 30 | 15 |
| 35 | 17.5 | 20 | 15 | 70 | 17.5 | 20 | 15 |
| 8.75 | 35 | 30 | 20 | 17.5 | 35 | 30 | 20 |
| 17.5 | 35 | 30 | 20 | 35 | 35 | 30 | 20 |
| 35 | 35 | 35 | 20 | 70 | 35 | 35 | 20 |

% Injury

| Application Rate (g/ha) | | LEFCH | |
|---|---|---|---|
| Compound C TEA | Penoxsulam | Ob | Ex |
| 35 | 0 | 50 | — |
| 70 | 0 | 95 | — |
| 0 | 8.75 | 0 | — |
| 35 | 8.75 | 80 | 50 |
| 70 | 8.75 | 100 | 95 |

TABLE 103

Synergistic Activity of Herbicidal Compositions on Key Sedge Weeds in Transplanted Paddy Rice
% Injury

| Application Rate (g/ha) | | CYPES | | CYPIR | | ELOKU | | Application Rate (g/ha) | | ELOKU | |
|---|---|---|---|---|---|---|---|---|---|---|---|
| Compound A TEA | Penoxsulam | Ob | Ex | Ob | Ex | Ob | Ex | Compound C TEA | Penoxsulam | Obs | Ex |
| 35 | 0 | 20 | — | 10 | — | 30 | — | 35 | 0 | 0 | — |
| 70 | 0 | 50 | — | 20 | — | 20 | — | 70 | 0 | 50 | — |
| 0 | 8.75 | 40 | — | 70 | — | 0 | — | 0 | 8.75 | 0 | — |
| 35 | 8.75 | 60 | 52 | 100 | 73 | 60 | 30 | 35 | 8.75 | 60 | 0 |
| 70 | 8.75 | 95 | 70 | 90 | 76 | 80 | 20 | 70 | 8.75 | 80 | 50 |

TABLE 104

Synergistic Activity of Herbicidal Compositions on a Key Broadleaf Weed in Transplanted Paddy Rice
% Injury

| Application Rate (g/ha) | | SPDZE | |
|---|---|---|---|
| Compound C TEA | Cyhalofop-butyl | Ob | Ex |
| 35 | 0 | 50 | — |
| 70 | 0 | 80 | — |
| 0 | 90 | 0 | — |
| 35 | 90 | 70 | 50 |
| 70 | 90 | 95 | 80 |

TABLE 105

Synergistic Activity of Herbicidal Compositions on Key Grass Weeds in Transplanted Paddy Rice
% Injury

| Application Rate (g/ha) | | ECHCG | | LEFCH | | Application Rate (g/ha) | | ECHCG | | LEFCH | |
|---|---|---|---|---|---|---|---|---|---|---|---|
| Compound A TEA | Cyhalofop-butyl | Ob | Ex | Ob | Ex | Compound C TEA | Cyhalofop-butyl | Ob | Ex | Ob | Ex |
| 35 | 0 | 0 | — | 80 | — | 35 | 0 | 0 | — | 50 | — |
| 70 | 0 | 50 | — | 99 | — | 70 | 0 | 25 | — | 95 | — |
| 0 | 90 | 50 | — | 50 | — | 0 | 90 | 50 | — | 50 | — |
| 0 | 180 | 75 | — | | | 0 | 180 | 95 | — | | |
| 35 | 90 | 100 | 25 | 100 | 75 | 35 | 90 | 100 | 50 | 100 | 75 |
| 70 | 90 | 100 | 75 | 100 | 100 | 70 | 90 | 100 | 63 | 100 | 98 |
| 35 | 180 | 100 | 75 | | | 35 | 180 | 100 | 95 | | |
| 70 | 180 | 100 | 98 | | | 70 | 180 | 100 | 96 | | |

TABLE 106

Synergistic Activity of Herbicidal Compositions on Key Sedge Weeds in Transplanted Paddy Rice
% Injury

| Application Rate (g/ha) | | CYPES | | CYPIR | | FIMMI | | SCPMA | | SCPJU | |
|---|---|---|---|---|---|---|---|---|---|---|---|
| Compound A TEA | Cyhalofop-butyl | Ob | Ex | Ob | Ex | Ob | Ex | Ob | Ex | Ob | Ex |
| 35 | 0 | 25 | — | 10 | — | 0 | — | 0 | — | 85 | — |
| 70 | 0 | 50 | — | 20 | — | 0 | — | 50 | — | 95 | — |
| 0 | 90 | 0 | — | 0 | — | 0 | — | 0 | — | 0 | — |
| 35 | 90 | 100 | 25 | 40 | 10 | 40 | 10 | 10 | 0 | 100 | 85 |
| 70 | 90 | 100 | 50 | 100 | 20 | 100 | 60 | 100 | 50 | 100 | 95 |

TABLE 106-continued

Synergistic Activity of Herbicidal Compositions on Key Sedge Weeds in Transplanted Paddy Rice
% Injury

| Application Rate (g/ha) | | CYPES | | CYPIR | | FIMMI | | SCPMA | |
|---|---|---|---|---|---|---|---|---|---|
| Compound C TEA | Cyhalofop-butyl | Ob | Ex | Ob | Ex | Ob | Ex | Ob | Ex |
| 35 | 0 | 0 | — | 20 | — | 0 | — | 0 | — |
| 70 | 0 | 40 | — | 60 | — | 0 | — | 0 | — |
| 0 | 90 | 0 | — | 0 | — | 0 | — | 0 | — |
| 35 | 90 | 100 | 0 | 100 | 20 | 100 | 0 | 20 | 0 |
| 70 | 09 | 100 | 40 | 100 | 60 | 100 | 0 | 20 | 0 |

TABLE 107

Synergistic Activity of Herbicidal Compositions on Key Sedge Weeds in Transplanted Paddy Rice
% Injury

| Application Rate (g/ha) | | FIMMI | | SCPJU | | Application Rate (g/ha) | | FIMMI | | SCPJU | |
|---|---|---|---|---|---|---|---|---|---|---|---|
| Compound A Methyl | Fenoxaprop-p-ethyl | Ob | Ex | Ob | Ex | Compound A TEA | Fenoxaprop-p-ethyl | Ob | Ex | Ob | Ex |
| 17.5 | 0 | 20 | — | 90 | — | 17.5 | 0 | 30 | — | 60 | — |
| 0 | 35 | 0 | — | 0 | — | 0 | 35 | 0 | — | 0 | — |
| 17.5 | 35 | 100 | 20 | 95 | 90 | 17.5 | 35 | 100 | 30 | 80 | 60 |

TABLE 108

Synergistic Activity of Herbicidal Compositions on a Key Broadleaf Weed in Transplanted Paddy Rice
% Injury

| Application Rate (g/ha) | | MASCR | | Application Rate (g/ha) | | MASCR | |
|---|---|---|---|---|---|---|---|
| Compound A Methyl | Quinclorac | Ob | Ex | Compound A TEA | Quinclorac | Ob | Ex |
| 17.5 | 0 | 0 | — | 17.5 | 0 | | |
| 35 | 0 | 50 | — | 35 | 0 | 60 | — |
| 0 | 140 | 0 | — | 0 | 140 | 0 | — |

TABLE 108-continued

Synergistic Activity of Herbicidal Compositions on a Key Broadleaf Weed in Transplanted Paddy Rice
% Injury

| Application Rate (g/ha) | | MASCR | | Application Rate (g/ha) | | MASCR | |
|---|---|---|---|---|---|---|---|
| Compound A Methyl | Quinclorac | Ob | Ex | Compound A TEA | Quinclorac | Ob | Ex |
| 17.5 | 140 | 40 | 0 | 17.5 | 140 | 80 | 60 |
| 35 | 140 | 60 | 50 | 35 | 140 | 80 | 60 |

TABLE 109

Synergistic Activity of Herbicidal Compositions on Key Grass Weeds in Transplanted Paddy Rice
% Injury

| Application Rate (g/ha) | | LEFCH | | Application Rate (g/ha) | | LEFCH | | ECHCG | |
|---|---|---|---|---|---|---|---|---|---|
| Compound A Methyl | Quinclorac | Ob | Ex | Compound A TEA | Quinclorac | Ob | Ex | Ob | Ex |
| 17.5 | 0 | 10 | — | 17.5 | 0 | 10 | — | 10 | — |
| 35 | 0 | 20 | — | 35 | 0 | 15 | — | 80 | — |
| 0 | 140 | 0 | — | 0 | 140 | 0 | — | 0 | — |
| 17.5 | 140 | 20 | 10 | 17.5 | 140 | 60 | 10 | 100 | 10 |
| 35 | 140 | 45 | 20 | 35 | 140 | 70 | 15 | 100 | 80 |

TABLE 110

Synergistic Activity of Herbicidal Compositions on Key Sedge Weeds in Transplanted Paddy Rice
% Injury

| Application Rate (g/ha) | | | | | | Application Rate (g/ha) | | | | | |
|---|---|---|---|---|---|---|---|---|---|---|---|
| Compound | | CYPES | | FIMMI | | Compound | | CYPES | | FIMMI | |
| A Methyl | Quinclorac | Ob | Ex | Ob | Ex | A TEA | Quinclorac | Ob | Ex | Ob | Ex |
| 17.5 | 0 | 50 | — | 20 | — | 17.5 | 0 | 30 | — | 30 | — |
| 0 | 140 | 0 | — | 0 | — | 0 | 140 | 0 | — | 0 | — |
| 17.5 | 140 | 100 | 50 | 100 | 20 | 17.5 | 140 | 100 | 96 | 60 | 30 |

TABLE 111

Synergistic Activity of Herbicidal Compositions on Key Grass Weeds in Transplanted Paddy Rice
% Injury

| Application Rate (g/ha) | | | | | |
|---|---|---|---|---|---|
| Compound A | | ECHOR | | ECHCG | |
| TEA | Quinclorac | Ob | Ex | Ob | Ex |
| 35 | 0 | 10 | — | 10 | — |
| 0 | 70 | 0 | — | 0 | — |
| 35 | 70 | 35 | 10 | 35 | 10 |

TABLE 112

Synergistic Activity of Herbicidal Compositions on a Key Sedge Weed in Transplanted Paddy Rice
% Injury

| Application Rate (g/ha) | | | | Application Rate (g/ha) | | | |
|---|---|---|---|---|---|---|---|
| Compound | | CYPES | | Compound | | CYPES | |
| A Methyl | Norflurazon | Ob | Ex | A TEA | Norflurazon | Ob | Ex |
| 35 | 0 | 60 | — | 17.5 | 0 | 30 | — |
| 0 | 70 | 0 | — | 35 | 0 | 70 | — |
| 35 | 70 | 95 | 60 | 0 | 70 | 0 | — |
| | | | | 17.5 | 70 | 50 | 30 |
| | | | | 35 | 70 | 100 | 70 |

TABLE 113

Synergistic Activity of Herbicidal Compositions on a Key Grass Weed in Transplanted Paddy Rice
% Injury

| Application Rate (g/ha) | | | | Application Rate (g/ha) | | | |
|---|---|---|---|---|---|---|---|
| Compound | | ECHOR | | Compound | | ECHOR | |
| A Methyl | Sulcotrione | Ob | Ex | A TEA | Sulcotrione | Ob | Ex |
| 17.5 | 0 | 0 | — | 17.5 | 0 | 0 | — |
| 35 | 0 | 10 | — | 35 | 0 | 10 | — |
| 0 | 70 | 10 | — | 0 | 70 | 10 | — |
| 17.5 | 70 | 25 | 10 | 17.5 | 70 | 30 | 10 |
| 35 | 70 | 85 | 19 | 35 | 70 | 60 | 19 |

IPOHE = *Ipomoea hederacea*
POLPE = *Polygonum persicaria*
SPDZE = *Sphenoclea zeylanica*
ECHCG = *Echinochloa crus-galli*
ISCRU = *Ischaemum rugosum*

TABLE 113-continued

Synergistic Activity of Herbicidal Compositions on a Key Grass Weed in Transplanted Paddy Rice
% Injury

| Application Rate (g/ha) | | | | Application Rate (g/ha) | | | |
|---|---|---|---|---|---|---|---|
| Compound | | ECHOR | | Compound | | ECHOR | |
| A Methyl | Sulcotrione | Ob | Ex | A TEA | Sulcotrione | Ob | Ex |

CYPES = *Cyperus esculentus*
ELOKU = *Eleocharis kuroguwai*
SCPJU = *Scirpus juncoides*
Ob = observed values
Ex = expected, calculated values
DAA = days after application
MASCR = *Marsilea crenata*
POLPY = *Polygonum pensylvanicum*
DIGSA = *Digitaria sanguinalis*
ECHOR = *Echinocloa oryzoides*
LEFCH = *Leptochloa chinensis*
CYPIR = *Cyperus iria*
FIMMI = *Fimbristylis miliacea*
SCPMA = *Scirpus maritimus*

What is claimed is:

1. A synergistic herbicidal mixture comprising an herbicidally effective amount of (a) a first herbicide selected from the group of a pyridine or a pyrimidine carboxylic acid of the formula (I)

(I)

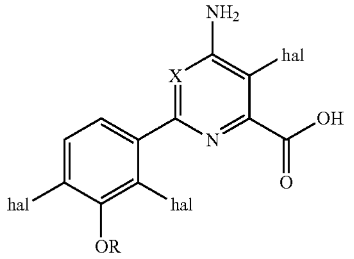

wherein X represents CH, hal represents F, Cl or Br, and R represents methyl or ethyl, or an agriculturally acceptable salt, ester or amide thereof, and (b) a second herbicide selected from the group consisting of aminopyralid, bispyribac, cyhalofop, triclopyr and mixtures thereof; wherein the weight ratio of the first herbicide to aminopyralid ranges from 3.5:1 to 14:1;

the weight ratio of the first herbicide to bispyribac ranges from 1:6.39 to 2.5:1;

the weight ratio of the first herbicide to cyhalofop ranges from 70:90 to 4.38:200; or the weight ratio of the first herbicide to triclopyr ranges from 1:16 to 1:32.

2. The mixture of claim 1 in which, for the compound of Formula I, X represents CH hal represents F or Cl and R represents methyl.

3. The mixture of claim 1 in which the pyridine carboxylic acid of the formula (I) is 4-amino-3-chloro-6-(4-chloro-2-fluoro-3-methoxy-phenyl)pyridine-2-carboxylic acid, or an agriculturally acceptable salt or ester thereof.

4. The mixture of claim 1 further comprising an herbicide safener.

5. The mixture of claim 4 in which the herbicide safener is cloquintocet.

6. The mixture of claim 4 in which the herbicide safener is mefenpyr-diethyl.

7. An herbicidal composition comprising an herbicidally effective amount of the herbicidal mixture of claim 1 and an agriculturally acceptable adjuvant or carrier.

8. The mixture of claim 1, wherein the second herbicide is aminopyralid.

9. The mixture of claim 1, wherein the second herbicide is cyhalofop.

10. The mixture of claim 1, wherein the second herbicide is triclopyr.

11. A method of controlling undesirable vegetation which comprises contacting the vegetation or the locus thereof with or applying to the soil or water to control the emergence or growth of vegetation an herbicidally effective amount the herbicidal mixture of claim 1.

12. The method of claim 11, wherein the undesirable vegetation is controlled in cereals.

13. The method of claim 11, wherein the undesirable vegetation is controlled in rice.

* * * * *